United States Patent [19]

Kalopissis et al.

[11] 4,200,432
[45] Apr. 29, 1980

[54] DYE COMPOSITION CONTAINING OXIDATION DYE AND DIPHENYLAMINE

[75] Inventors: Gregoire Kalopissis, Neuilly-sur-Seine; Andree Bugaut, Boulogne-Billancourt; Francoise Estradier, Paris, all of France

[73] Assignee: L'Oreal, Paris, France

[21] Appl. No.: 853,813

[22] Filed: Nov. 21, 1977

Related U.S. Application Data

[63] Continuation-in-part of Ser. No. 551,637, Feb. 21, 1975, abandoned.

[30] Foreign Application Priority Data

Feb. 22, 1974 [LU] Luxembourg .................. 69458

[51] Int. Cl.² ................................................ A61K 7/13
[52] U.S. Cl. ........................................ 8/10.2; 8/11; 8/32
[58] Field of Search ................ 8/10.2, 11, 32; 260/571

[56] References Cited

U.S. PATENT DOCUMENTS

| | | | |
|---|---|---|---|
| 2,101,879 | 12/1937 | Strouse | 260/571 |
| 2,692,262 | 10/1954 | Bosshard | 260/571 |
| 3,214,472 | 10/1965 | Charle et al. | 260/571 |

FOREIGN PATENT DOCUMENTS

| | | | |
|---|---|---|---|
| 2145724 | 2/1973 | France | 8/10.2 |
| 2174473 | 10/1973 | France | 8/10.2 |

*Primary Examiner*—Norman Morgenstern
*Assistant Examiner*—Vera C. Clarke
*Attorney, Agent, or Firm*—Cushman, Darby & Cushman

[57] ABSTRACT

A hair dye composition comprising at least one oxidation dye and at least one diphenylamine of the formula

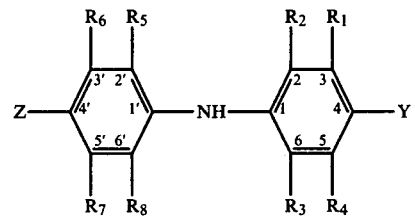

wherein
- $R_1$ and $R_4$ each independently represent hydrogen, halogen, lower alkyl having 1–6 carbon atoms, lower alkoxy having 1–6 carbon atoms, acylamino or ureido;
- $R_2$ and $R_3$ each independently represent hydrogen, halogen, lower alkyl having 1–6 carbon atoms, lower alkoxy having 1–6 carbon atoms, amino, N-alkylamino wherein the alkyl has 1–6 carbon atoms, N-hydroxyalkylamino wherein the alkyl has 1–6 carbon atoms, acylamino, N-carbamylalkylamino wherein the alkyl has 1–6 carbon atoms or ureido;
- $R_5$ represents hydrogen, halogen, lower alkyl having 1–6 carbon atoms or lower alkoxy having 1–6 carbon atoms;
- $R_6$, $R_7$ and $R_8$, each independently represent hydrogen, halogen, lower alkyl having 1–6 carbon atoms or lower alkoxy having 1–6 carbon atoms;
- Y represents hydroxy or amino; and
- Z represents hydroxy or

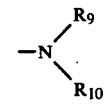

wherein
- $R_9$ and $R_{10}$ each independently represents hydrogen, lower alkyl containing 1–6 carbon atoms, hydroxyalkyl containing 1–6 carbon atoms, carbamyl alkyl wherein the alkyl has 1–6 carbon atoms, amino alkyl wherein the alkyl has 1–6 carbon atoms, monoalkylamino alkyl wherein each alkyl has 1–6 carbon atoms, dialkylamino alkyl wherein each alkyl has 1–6 carbon atoms, acylaminoalkyl wherein the alkyl has 1–6 carbon atoms, alkylsulfonamido alkyl wherein each alkyl has 1–6 carbon atoms, arylsulfonamidoalkyl wherein the alkyl has 1–6 carbon atoms, sulfoalkyl wherein the alkyl has 1–6 carbon atoms, piperidinoalkyl wherein the alkyl has 1–6 carbon atoms or morpholinoalkyl wherein the alkyl has 1–6 carbon atoms; or a salt thereof.

34 Claims, No Drawings

DYE COMPOSITION CONTAINING OXIDATION DYE AND DIPHENYLAMINE

This application is a continuation-in-part of application Ser. No. 551,637, filed Feb. 21, 1975, now abandoned.

The present invention relates to dye compositions containing oxidation dyes and diphenylamines.

It is known to use for the dyeing of keratinic fibers, and particularly living human hair, dye compositions containing oxidation dyes in the presence of an oxidizing agent.

In procedures for employing oxidation dyes, the dye composition containing the same is prepared at the moment of application of the same to the hair by the addition of an oxidizing agent, such as hydrogen peroxide, to an ammoniacal solution of one or more oxidation bases. These oxidation bases are diamines or diaminophenols or aminophenols having amino or hydroxy groups which are para or ortho to one another, such as paraphenylene diamines or paraaminophenols, or to their derivatives. Further, a mixture of such oxidation bases can be used with couplers which are meta diamines, meta aminophenols and meta diphenols, or derivatives of these compounds such as meta acetylaminophenols, meta ureido phenols and pyrazolones or even pyridine derivatives such as 2,6-diamino pyridine.

Generally, such dye mixtures nearly always contain oxidation bases such as paratolylene diamine and para aminophenol, and couplers such as meta aminophenol, meta diamino anisole and resorcinol.

The oxidation bases react in an ammoniacal oxidizing medium with the couplers to produce colors which impart to the fibers being dyed therewith a variety of shades depending upon the chemical configuration of the two initial reactants.

In such a system the resulting color which is obtained depends essentially on the coupling speed of the different possible combinations of oxidation bases and couplers present in the system.

The introduction of a new oxidation base and a new coupler, which lead to a shade, either particularly stable to light and to weather, or particularly aesthetic, in a simple coupling, does not lead necessarily to the clear apparition of the color or of the quality expected if the coupling speed, or the oxidation potential of the other components in the formulation do not permit that this coupling takes place sufficiently rapidly to be visible.

Further, in a certain number of instances, the oxidation bases and couplers employed are not sufficient to obtain all the shades desired such as certain shades with glints, and there is also required to be used a direct dye. These direct dyes belong generally to the series of nitro benzene dyes, but can also belong to other series.

However, the introduction of these dyes presents a certain number of disadvantages characterized by a lack in these oxidation dyes, on the one hand, of simultaneous action and, on the other hand, a lack of stability to light, weather and different capillary treatments.

Further, it is also known that in an ammoniacal oxidizing medium, the oxidation bases and couplers utilized produce, depending on the nature thereof, iodophenol, iodoaniline and indamine dyes.

The synthetis of these compounds and their leuco derivatives, as well as their use for dyeing hair has already been the object of numerous commonly assigned patents.

It has been discovered that by combining in the dyeing of hair, the diphenylamine leuco derivatives of indoanilines, indophenols and indamines with oxidation dyes, not only are colors obtained which have not been achieved by classically known systems but also the colors achieved have a clear greater luminosity than heretofore attainable. Moreover, the simultaneous action obtained is remarkable being given that all the dyes participating in the coloration belong to a homogeneous family.

It has also been discovered that the stability of the color obtained on the hair, i.e. its stability to washing, to light and to heat has been surprisingly and significantly improved.

The present invention relates to dye compositions for keratinic fibers containing at least one leuco derivative of indamine, indoaniline or indophenol and at least one oxidation dye which is preferably a paraphenylenediamine, a paraaminophenol or a heterocyclic base.

The diphenylamines usefully employed in the composition of the present invention have the formula

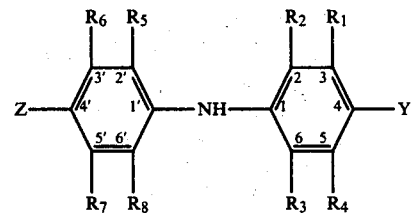

wherein $R_1$ and $R_4$ each independently represent a member selected from the group consisting of hydrogen, halogen, lower alkyl having 1–6 carbon atoms, lower alkoxy having 1–6 carbon atoms, acylamino and ureido, $R_2$ and $R_3$ each independently represent a member selected from the group consisting of hydrogen, halogen, lower alkyl having 1–6 carbon atoms, lower alkoxy having 1–6 carbon atoms, amino, N-alkylamino wherein the alkyl moiety has 1–6 carbon atoms, N-hydroxyalkylamino wherein the alkyl moiety has 1–6 carbon atoms, acylamino, N-carbamylalkylamino wherein the alkyl moiety has 1–6 carbon atoms and ureido;

$R_5$ represents a member selected from the group consisting of hydrogen, halogen, lower alkyl having 1–6 carbon atoms and lower alkoxy having 1–6 carbon atoms;

$R_6$, $R_7$ and $R_8$ each independently represent a member selected from the group consisting of hydrogen, halogen, lower alkyl having 1–6 carbon atoms and lower alkoxy having 1–6 carbon atoms;

Y represents a member selected from the group consisting of hydroxy and amino; and Z represents a member selected from the group consisting of hydroxy and

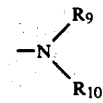

wherein $R_9$ and $R_{10}$ each independently represent a member selected from the group consisting of hydrogen, lower alkyl containing 1-6 carbon atoms, hydroxyalkyl containing 1-6 carbon atoms, carbamylalkyl wherein the alkyl moiety has 1-6 carbon atoms, aminoalkyl wherein the alkyl moiety has 1-6 carbon toms, monoalkyl aminoalkyl wherein each of the alkyl moieties has 1-6 carbon atoms, dialkylaminoalkyl wherein each of the alkyl moieties has 1-6 carbon atoms, acylaminoalkyl wherein the alkyl moiety has 1-6 carbon atoms, alkylsulfonamido alkyl wherein each of the alkyl moieties has 1-6 carbon atoms, arylsulfonamido alkyl wherein the aryl moiety is preferably phenyl and the alkyl moiety has 1-6 carbon atoms, sulfoalkyl wherein the alkyl moiety has 1-6 carbon atoms, piperidinoalkyl wherein the alkyl moiety has 1-6 carbon atoms and morpholino alkyl wherein the alkyl moiety has 1-6 carbon atoms, with the proviso that when Z is OH and Y is amino, and $R_1$ and $R_4$ are hydrogen or alkyl, or when Z is OH, Y is amino, $R_1$ or $R_4$ is alkoxy and $R_5$, $R_6$, $R_7$, $R_8$ are hydrogen, alkyl or halogen, at least one being different from hydrogen, $R_2$ and $R_3$ are other than amino or acetylamino.

The diphenylamines can also be utilized in the form of their salts such as the hydrochloride, hydrobromide, sulfate or phosphate thereof.

Representative paraphenylenediamines usefully employed in the compositions of the present invention include primary, secondary or tertiary paraphenylenediamines, optionally substituted on the phenyl ring. Preferably these paraphenylenediamines have the formula

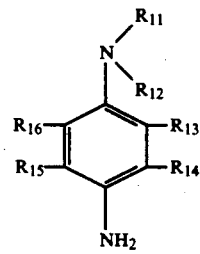

wherein $R_{11}$ and $R_{12}$ each independently represent a member selected from the group consisting of hydrogen, straight or branch chained lower alkyl having 1-6 carbon atoms, hydroxyalkyl having 1-6 carbon atoms and one or more hydroxy groups, piperidinoalkyl wherein the alkyl moiety has 1-6 carbon atoms, carbamylalkyl wherein the alkyl moiety has 1-6 carbon atoms, dialkyl carbamylalkyl wherein each alkyl moiety has 1-6 carbon atoms, amino alkyl having 1-6 carbon atoms, monoalkylamino alkyl wherein each alkyl moiety has 1-6 carbon atoms, dialkylaminoalkyl wherein each alkyl moiety has 1-6 carbon atoms, ω-aminosulfonylalkyl wherein the alkyl moiety has 1-6 carbon atoms, carboxyalkyl wherein the alkyl moiety has 1-6 carbon atoms, alkyl sulfonamidoalkyl wherein each alkyl moiety has 1-6 carbon atoms, arylsulfonamidoalkyl wherein the alkyl moiety has 1-6 carbon atoms, morpholinoalkyl wherein the alkyl moiety has 1-6 carbon atoms, acylaminoalkyl wherein the alkyl moiety has 1-6 carbon atoms, sulfoalkyl wherein the alkyl moiety has 1-6 carbon atoms, and sulfonamidoalkyl wherein the alkyl moiety has 1-6 carbon atoms, or $R_{11}$ and $R_{12}$ together with the nitrogen atom to which they are attached form a member selected from the group consisting of morpholino and piperidinyl; and $R_{13}$, $R_{14}$, $R_{15}$ and $R_{16}$ each independently represent a member selected from the group consisting of hydrogen, halogen, lower alkyl containing 1-6 carbon atoms and lower alkoxy containing 1-6 carbon atoms.

In the above paraphenylenediamines, the lower alkyl and lower alkoxy substituents or moieties contain, preferably, 1-4 carbon atoms and the halogen substituent can be fluorine, bromine and preferably chlorine.

Particularly efficacious paraphenylenediamines usefully employed in the composition of the present invention include: paraphenylenediamine, paratolylenediamine, methoxy paraphenylenediamine, chloro paraphenylenediamine, 2,6-dimethyl paraphenylenediamine, 2,5-dimethyl paraphenylenediamine, 2-methyl-5-methoxy parphenylenediamine, 2,6-dimethyl-5-methoxy paraphenylenediamine, N,N-dimethyl paraphenylenediamine, 3-methyl-4-amino-N,N-(diethyl) aniline, N,N-(di-β-hydroxyethyl) paraphenylenediamine, 3-methyl-4-amino-N,N-(di-β-hydroxyethyl) aniline, 3-chloro-4-amino-N,N-(di-β-hydroxyethyl) aniline, 4-amino-N,N-(ethyl, carbamylmethyl) aniline, 3-methyl-4-amino-N,N-(ethyl, carbamylmethyl) aniline, 4-amino-N,N-(ethyl, morpholinoethyl) aniline, 3-methyl-4-amino-N,N-(ethyl, morpholinoethyl) aniline, 4-amino-N,N-(ethyl, acetylaminoethyl) aniline, 3-methyl-4-amino-N,N-(ethyl, acetylaminoethyl) aniline, 4-amino-N,N-(ethyl, mesylaminoethyl) aniline, 3-methyl-4-amino-N,N-(ethyl, mesylaminoethyl) aniline, 4-amino-N,N-(ethyl, β-sulfoethyl) aniline, 3-methyl-4-amino-N,N-(ethyl, β-sulfoethyl) aniline, N-[(4'-amino)phenyl] morpholine, N-[(4'-amino) phenyl] piperidine, 4-amino-N,N-(ethyl, piperidinoethyl) aniline, 3-methyl-4-amino-N-methyl aniline, 2-chloro-4-amino-N,N-(ethyl, sulfonamidoethyl) aniline, 2-chloro-4-amino-N-(ethyl) aniline and 2-methyl-4-amino-N-(β-hydroxyethyl) aniline.

These paraphenylenediamines can be introduced into the dye composition in the free base form or salified form, for example in the form of the mono-, di- or tri-hydrochloride, hydrobromide or sulfate thereof.

Representative other oxidation bases usefully employed in the present invention include paraaminophenol, 2-methyl-4-aminophenol, 3-methyl-4-aminophenol, 2-chloro-4-aminophenol, 3-chloro-4-aminophenol, 2,6-dimethyl-4-aminophenol, 3,5-dimethyl-4-aminophenol, 2,3-dimethyl-4-aminophenol, 2,5-dimethyl-4-aminophenol, 2,5-diamino pyridine, 2-dimethylamino-5-amino pyridine, 2-diethylamino-5-amino pyridine, 3-methyl-7-amino phenomorpholine and 5-amino indole.

The dye composition of the present invention in addition to containing one or more diphenylamines and one or more oxidation bases, can also contain couplers. The couplers usefully employed in the present invention have the formula

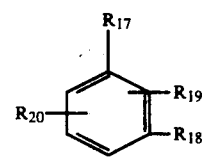

wherein

R$_{17}$ and R$_{18}$ each independently represent a member selected from the group consisting of hydroxy and —NHR wherein R represents a member selected from the group consisting of hydrogen, acyl, ureido, carbalkoxy wherein the alkoxy moiety has 1-6 carbon atoms, carbamylalkyl wherein the alkyl moiety has 1-6 carbon atoms, alkyl having 1-6 carbon atoms, dialkylcarbamylalkyl wherein each alkyl moiety has 1-6 carbon atoms and hydroxyalkyl having 1-6 carbon atoms; R$_{17}$ and R$_{18}$ each independently can also represent a member selected from the group of hydrogen, alkoxy containing 1-6 carbon atoms, alkyl containing 1-6 carbon atoms, with the proviso that at least one of R$_{17}$ and R$_{18}$ is hydroxy; and R$_{19}$ and R$_{20}$ each independently represent a member selected from the group consisting of hydrogen, straight or branched alkyl containing 1-6 carbon atoms, alkoxy containing 1-6 carbon atoms, halogen, amino, aminoalkyl wherein the alkyl moiety has 1-6 carbon atoms, acylamino and ureido.

Representative usefully employed couplers include resorcinol, meta-aminophenol, 2,4-diamino anisole, 2-methyl-5-ureido phenol, 2,6-dimethyl aminophenol, 2-methyl-5-acetylaminophenol, 2,6-dimethyl-5-acetylaminophenol and 3-amino-4-methoxy phenol.

Other couplers usefully employed in the composition of the present invention include such heterocyclic compounds as 6-hydroxy phenomorpholine, 6-amino phenomorpholine, pyridine derivatives, diketone compounds and pyrazolones.

Representative diketone compounds particularly useful in the present invention include those having the formula

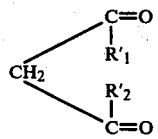

wherein

R′$_1$ and R′$_2$ each independently represent a member selected from the group consisting of alkyl having 1-6 carbon atoms, preferably 1-4 carbon atoms, alkoxy containing 1-6 carbon atoms, phenyl,

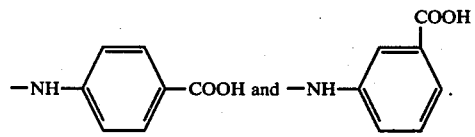

Representative pyrazolones usefully employed in the present invention include those having the formula

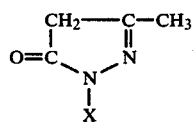

wherein

X represents a member selected from the group consisting of phenyl and phenyl substituted with a member selected from the group consisting of —SO$_3$H and halogen, said halogen being fluorine, bromine, or, preferably, chlorine.

The composition of the present invention can also contain, other than oxidation dyes, such dyes as azo dyes, anthraquinone dyes, nitrobenzene dyes, indamines, indoanilines and indophenols.

The cosmetic composition of the present invention can be provided in the form of an aqueous or hydroalcoholic, preferably an ethanolic or isopropanolic solution. The composition can also contain other solvents, preferably glycols such as butyl glycol, propylene glycol and the monomethyl ester of diethylene glycol.

The composition of the present invention can be provided in the form of a cream or gel.

Further the composition of the present invention can also include wetting agents or surface active agents such as the sulfates of fatty alcohols, ethanolamides of fatty acids, polyoxyethylenated fatty acids and alcohols, thickening agents such as carboxymethyl cellulose, higher fatty alcohols, polymers, perfumes, complexing agents, reducing agents, alkalizing agents such as ammonia and ethanolamines and acidifying agents such as phosphoric acid, lactic acid and acetic acid.

Representative polymers usefully employed in the composition of the present invention include cosmetic film-forming polymers such as polyvinylpyrrolidone, copolymers of vinylpyrrolidone and vinyl acetate, copolymers of vinyl acetate and an unsaturated carboxylic acid such as crotonic acid, copolymers resulting from the copolymerization of vinyl acetate, crotonic acid or an acrylic or methacrylic ester, copolymers resulting from the copolymerization of vinyl acetate and an alkylvinyl ether, copolymers resulting from the copolymerization of vinyl acetate, crotonic acid and a vinyl ester of a long carbon chain acid or again of an allyl or methallyl ester of a long carbon chain acid, copolymers resulting from the copolymerization of an ester derived from an unsaturated alcohol and a short carbon chain acid, from a short carbon chain unsaturated acid and from at least one ester derived from a short carbon chain saturated alcohol and from an unsaturated acid, and copolymers resulting from the copolymerization of at least one unsaturated ester and at least one unsaturated acid.

Representative preferred cosmetic film forming resins usefully employed in the composition of the present invention include polyvinylpyrrolidone having a molecular weight of 10,000 to 70,000, copolymers of 10% crotonic acid and 90% vinyl acetate having a molecular weight of 10,000 to 70,000, copolymers of vinylpyrrolidone and vinyl acetate having a molecular weight of 30,000 to 200,000, the ratio of VP:VA between 30:70 and 70:30, copolymers of maleic anhydride and methylvinyl ether in preferably a 1:1 mole ratio and having a specific viscosity ranging between 0.1 and 3.5 when measured at 25° C. at a concentration of 1 g in 100 cc of methylethylketone; the monoethyl, monoisopropyl or monobutyl esters of said copolymer of maleic anhydride and methylvinyl ether, copolymer of maleic anhydride and butylvinyl ether, the mole ratio of maleic anhydride to butylvinyl ether being 1:1, terpolymers of methyl methacrylate (15-25%), stearyl methacrylate (18-28%) and dimethyl methacrylate (52-62%) and terpolymers of vinyl acetate (75-85%), allyl stearate (10-20%) and allyloxyacetic acid (3-10%).

The concentration of the diphenylamines used in the composition of the present invention can range between about 0.005 to 5 percent, and preferably between about 0.01 to 3 percent, by weight of the total composition.

The pH of the dye composition of the present invention can range between 5 to 11 and preferably between 8 to 10.5.

The dye composition of the present invention can be utilized in accordance with conventional procedures after the addition thereto of an oxidizing agent. The resulting mixture is then applied to the fibers or hair to be dyed and it is permitted to remain in contact therewith for a period ranging from 5 to 45 minutes, preferably 15–30 minutes, after which the fibers or hair are rinsed and dried.

The concentration of the oxidation base in the composition of the present invention ranges between about 0.001 to 5 and preferably between about 0.03 to 2 percent by weight of the total composition while that of the coupler ranges between about 0.001 to 5 and preferably between about 0.015 to 2 percent by weight of the total composition. The oxidizing agent is employed in amounts ranging from about 1–3 parts by weight thereof per part by weight of the dye composition of the present invention.

The oxidizing agent generally employed is hydrogen peroxide at a concentration ranging between 2.4% (8 volumes) to 9% (30 volumes). Urea peroxide and persalts such as persulfates and perborates can also be employed.

The composition of the present invention can also be provided in the form of an aerosol packaged in a two compartment aerosol container, employing conventional aerosol propellants under pressure.

The following non-limiting examples illustrate the present invention.

EXAMPLE 1

The following dye composition is prepared:

| | |
|---|---|
| Paratolylenediamine | 0.5 g |
| 2-carbamylmethyl-amino-4-hydroxy-4'-N,N-(di-β hydroxyethyl) amino-5-methyl diphenylamine | 0.4 g |
| Nonyl phenol oxyethylenated with 4 moles of ethylene oxide (sold under the mark Remcopal 334) | 22 g |
| Nonyl phenol oxyethylenated with 9 moles of ethylene oxide (sold under the mark Remcopal 349) | 22 g |
| Butyl glycol | 8 g |
| Propylene glycol | 8 g |
| Solution of sodium bisulfite (35° Bé) | 1 g |
| Ammonia (22° Bé) | 10 cc |
| Water, q.s.p. | 100 g |

To 50 g of this dye composition there are added 50 g of hydrogen peroxide (20 volumes). The resulting mixture in the form of a gel having a pH of 9.8 is then applied to the hair to be dyed. The mixture is permitted to remain in contact with the hair for a period of 20 minutes after which the hair is rinsed and shampooed. There is thus obtained on natural blond hair having 80 percent white hair a slightly iridescent ash blond coloration.

The same composition but without the said diphenylamine, under the same conditions, provides a natural blond coloration.

EXAMPLE 2

The following dye composition is prepared:

| | |
|---|---|
| Methoxy paraphenylenediamine | 0.3 g |
| 2-acetylamino-3,5-dimethyl-4-hydroxy-4'-N,N-(di-β-hydroxyethyl) amino diphenylamine | 0.2 g |
| 3,5-dimethyl-4,4'-dihydroxy diphenylamine | 0.2 g |
| Nonyl phenol oxyethylenated with 4 moles of ethylene oxide (sold under the mark Remcopal 334) | 22 g |
| Nonyl phenol oxyethylenated with 9 moles of ethylene oxide (sold under the mark Remcopal 349) | 22 g |
| Butyl glycol | 8 g |
| Propylene glycol | 8 g |
| Solution of sodium bisulfite (35° Bé) | 1 g |
| Ammonia, 22° Bé | 10 cc |
| Water, q.s.p. | 100 g |

To 50 g of this composition there are added 50 g of hydrogen peroxide (8 volumes). The resulting mixture in the form of a gel having a pH of 9.6 is then applied to the hair to be dyed. The mixture is permitted to remain in contact with the hair for a period of 5 minutes, after which the hair is rinsed and shampooed. There is thus obtained on very light blond hair (bleached) a light ash blond coloration. When this same mixture is applied to 100% white hair and the contact time therewith is 15 minutes, the resulting coloration imparted to such hair is a very luminous silver gray.

To 50 g of the same composition there are added 50 g of water containing 0.5 g of ammonium persulfate. The resulting mixture is a gel having a pH of 9.8. Immediately after preparing this gel the same is applied to hair to be dyed and the following results are obtained, after rinsing and shampooing:

(1) on bleached hair and with a contact time of 5 minutes, a pastel ash beige coloration is achieved;

(2) on natural blond hair with 80% white hair and with a contact time of 15 minutes, a flat yellow coloration is achieved.

EXAMPLE 3

The following dye composition is prepared:

| | |
|---|---|
| Paratolylenediamine | 0.5 g |
| 2-acetylamino-4-hydroxy-4'-N,N-(di-β-hydroxyethyl) amino-5-methyl diphenylamine | 0.3 g |
| 2-amino-3,5-dimethyl-4-hydroxy-4'-NN-(ethyl, carbamylmethyl) amino diphenylamine | 0.6 g |
| Nonyl phenol oxyethylenated with 4 moles of ethylene oxide (sold under the mark Remcopal 334) | 22 g |
| Nonyl phenol oxyethylenated with 9 moles of ethylene oxide (sold under the mark Remcopal 349) | 22 g |
| Butyl glycol | 8 g |
| Propylene glycol | 8 g |
| Solution of sodium bisulfite (35° Bé) | 1 g |
| Ammonia (22° Bé) | 10 cc |
| Water, q.s.p. | 100 g |

To 50 g of this composition there are added 50 g of hydrogen peroxide (8 volumes—2.4%). The resulting mixture which is a gel having a pH of 10.2 is then applied to the hair to be dyed. The following results, after rinsing and shampooing are obtained: on natural blond hair and with a contact time of 5 minutes, a very pretty iridescent ash coloration accompanied by a shiny lightness.

To 50 g of this same composition there are added 50 g of hydrogen peroxide (20 volumes). The resulting mixture which is a gel having a pH of 9.8 is then applied to natural deep blond hair having 80% white hair and is permitted to remain in contact therewith for 30 minutes. After rinsing and shampooing the hair, there is imparted thereto an ash blond coloration. Under the same conditions but using the above composition but without the said diphenylamines there is imparted to the same type of hair a neutral light blond coloration.

EXAMPLE 4

The following hair dye composition is prepared:

| | |
|---|---|
| Paraaminophenol | 0.4 g |
| Meta diamino anisol sulfate | 0.05 g |
| Resorcinol | 0.2 g |
| 2-ureido-4-hydroxy-4'-N,N-dimethylamino-5-methyl diphenylamine | 0.6 g |
| Nonyl phenol oxyethylenated with 4 moles of ethylene oxide (sold under the mark Remcopal 334) | 15 g |
| Nonyl phenol oxyethylenated with 9 moles of ethylene oxide (sold under the mark Remcopal 349) | 12 g |
| Oleic acid | 3 g |
| Cetyl trimethyl ammonium bromide | 3 g |
| Copra diethanolamide | 7 g |
| Ethyl alcohol (96° titer) | 8 g |
| Propylene glycol | 2 g |
| Butyl glycol | 5 g |
| Solution of sodium bisulfite (35° Bé) | 1 cc |
| Ammonia (22° Bé) | 12 cc |
| Water, q.s.p. | 100 g |

To 50 g of this composition there are added 50 g of hydrogen peroxide (20 volumes). The resulting mixture, which is a gel having a pH of 9.8, is then applied to hair to be dyed and the following results are achieved, after rinsing and shampooing.

(1) on natural deep blond hair with 80% white hair and with a contact time of 30 minutes, a golden blond coloration with very natural glints, whereas with the same composition except for the presence of the said diphenylamines and under the same conditions, there is obtained on white hair a coloration exhibiting excessive red glints; and (2) on hair bleached to a light blond coloration and with a contact time of 10 minutes, a pastel golden beige coloration is obtained.

EXAMPLE 5

The following dye composition is prepared:

| | |
|---|---|
| Paraaminophenol | 0.4 g |
| Meta diamino anisole sulfate | 0.05 g |
| Resorcinol | 0.2 g |
| 2-acetylamino-4-hydroxy-4'-N,N-dimethylamino diphenylamine | 0.4 g |
| Nonyl phenol oxyethylenated with 4 moles of ethylene oxide (sold under the mark Remcopal 334) | 15 g |
| Nonyl phenol oxyethylenated with 9 moles of ethylene oxide (sold under the mark Remcopal 349) | 12 g |
| Oleic acid | 3 g |
| Cetyl trimethyl ammonium bromide | 3 g |
| Copra diethanolamide | 7 g |
| Ethyl alcohol (96° titer) | 8 g |
| Propylene glycol | 2 g |
| Butyl glycol | 5 g |
| Solution of sodium bisulfite (35° Bé) | 1 cc |
| Ammonia (22° Bé) | 12 cc |
| Water, q.s.p. | 100 g |

To 50 g of this composition there are added 50 g of hydrogen peroxide (20 volumes). The resulting mixture which is a gel having a pH of 9.8 is then applied to natural blond hair and is permitted to remain in contact therewith for 20 minutes. After rinsing and shampooing there is obtained a natural very light blond coloration. Using this same composition without, however, the above diphenylamine and under the same conditions there is obtained a light blond coloration with reddish glints.

EXAMPLE 6

The following dye composition is prepared:

| | |
|---|---|
| Paratolylenediamine | 0.3 g |
| Paraaminophenol | 0.2 g |
| Resorcinol | 0.2 g |
| Meta aminophenol | 0.1 g |
| 2-acetylamino-3,5-dimethyl-4-hydroxy-4'-N,N-dimethylamine diphenylamine | 0.4 g |
| Nonyl phenyl oxyethylenated with 4 moles of ethylene oxide (sold under the mark Remcopal 334) | 15 g |
| Nonyl phenol oxyethylenated with 9 moles of ethylene oxide (sold under the mark Remcopal 349) | 12 g |
| Oleic acid | 3 g |
| Cetyl trimethyl ammonium bromide | 3 g |
| Copra diethanolamide | 7 g |
| Ethyl alcohol (96° titer) | 8 g |
| Propylene glycol | 2 g |
| Butyl glycol | 5 g |
| Solution of sodium bisulfite (35° Bé) | 1 cc |
| Ammonia (22° Bé) | 12 cc |
| Water, q.s.p. | 100 g |

To 50 g of this composition there are added 50 g hydrogen peroxide (20 volumes). The resulting mixture, which is a gel having a pH of 9.8 is then applied to the hair to be dyed. After rinsing and shampooing the following results are obtained:

(1) on natural blond hair with 80% white hair and with a contact time of 20 minutes, an ash blond coloration is achieved;

(2) on natural light chestnut hair and with a contact time of 20 minutes, a luminous slightly ashen light chestnut coloration is obtained; and (3) on blond hair with 80% white hair, with the same composition except without the diphenylamines and under the same conditions, a neutral light blond color is imparted to the hair.

EXAMPLE 7

The following dye composition is prepared:

| | |
|---|---|
| Paratolylenediamine | 0.3 g |
| Paraaminophenol | 0.2 g |
| Resorcinol | 0.2 g |
| Meta aminophenol | 0.1 g |
| 3,5-dimethyl-4-hydroxy-4'-N,N-dimethylamino diphenylamine | 0.8 g |
| Nonyl phenol oxyethylenated with 4 moles of ethylene oxide (sold under the mark Remcopal 334) | 15 g |
| Nonyl phenol oxyethylenated with 9 moles of ethylene oxide (sold under the mark Remcopal 349) | 12 g |
| Oleic acid | 3 g |
| Cetyl trimethyl ammonium bromide | 3 g |
| Copra diethanolamide | 7 g |
| Ethyl alcohol (96° titer) | 8 g |
| Propylene glycol | 2 g |
| Butyl glycol | 5 g |
| Solution of sodium bisulfite (35° Bé) | 1 cc |
| Ammonia (22° Bé) | 12 cc |
| Water, q.s.p. | 100 g |

To 50 g of this composition there are added 50 g of hydrogen peroxide (20 volumes). The resulting mixture which is a gel having a pH of 9.8 is then applied to hair to be dyed. After rinsing and shampooing the following results are obtained:

(1) on natural deep blond hair with 80% white hair, and with a contact time of 30 minutes, a deep ash blond coloration is achieved;

(2) on deep bright chestnut hair and with a contact time of 30 minutes, a very natural chestnut coloration is obtained; and (3) on light chestnut hair, with the same composition but without the diphenylamine and under the same conditions, a deep blond coloration with reddish glints is imparted to the hair.

EXAMPLE 8

The following dye composition is prepared:

| | |
|---|---|
| Paratolylenediamine | 0.5 g |
| 2-amino-3,5-dimethyl-4-hydroxy-4'-N,N-(ethyl, β-sulfoethyl) amino diphenylamine | 0.5 g |
| Cetyl stearyl alcohol | 20 g |
| Sodium cetyl stearyl sulfate | 2 g |
| Solution of sodium bisulfite (35° Bé) | 1 cc |
| Ammonia (20% solution) | 12 cc |
| Water, q.s.p. | 100 g |

To 50 g of this composition there are added 50 g of hydrogen peroxide (20 volumes). The resulting mixture which is a cream having a pH of 9.8 is applied to hair to be dyed. After rinsing and shampooing the following results are obtained.

(1) on deep natural blond hair with 80% white hair and with a contact time of 20 minutes, an iridescent maroon light chestnut coloration with good covering of the white hair is obtained;

(2) on natural chestnut hair with 80% white hair and with a contact time of 20 minutes, a moire maroon chestnut coloration is achieved;

(3) on deep natural blond hair with 80% white hair, with the same composition but without the diphenylamine and under the same conditions, a deep golden blond coloration is obtained;

(4) on natural chestnut hair with 80% white hair, with the same composition but without the diphenylamine and under the same conditions, a chestnut coloration with golden copper glints is imparted to the hair; and (5) on deep natural blond hair with 80% white hair, with the same composition except that the 0.5 g of paratolylene diamine is replaced by a mixture of 0.3 g of paraphenylenediamine and 0.2 g of N,N-dimethyl paraphenylenediamine and with a contact time of 20 minutes, a pearly ashen light chestnut coloration is imparted to the hair.

EXAMPLE 9

The following dye composition is prepared:

| | |
|---|---|
| Paraaminophenol | 0.4 g |
| Meta diamino anisole sulfate | 0.05 g |
| Resorcinol | 0.2 g |
| 2-acetylamino-2'3,5-trimethyl-4-hydroxy-4'-N,N-(ethyl, β-mesylamino ethyl) amino diphenylamine | 0.4 g |
| Cetyl stearyl alcohol | 30 g |
| Sodium cetyl stearyl sulfate | 3 g |
| Solution of sodium bisulfite (35° Bé) | 1 cc |
| Ammonia (20% solution) | 20 cc |
| Water, q.s.p. | 100 g |

To 30 g of this composition there are added 90 g of hydrogen peroxide (30 volumes). The resulting mixture, which is a cream having a pH of 9.5 is then applied to natural light chestnut hair and is permitted to remain in contact therewith for 40 minutes. After rinsing and shampooing there is imparted to the hair a natural, very light blond coloration. Using the same composition but without the diphenylamine gives a light blond coloration which is more flat than the coloration achieved immediately above with the diphenylamine containing composition.

EXAMPLE 10

The following dye composition is prepared:

| | |
|---|---|
| Paraaminophenol | 0.4 g |
| Meta diamino anisole sulfate | 0.05 g |
| Resorcinol | 0.2 g |
| 2-ureido-2'-methyl-4-hydroxy-4'-N,N-(ethyl, carbamylmethyl) amino diphenylamine | 0.4 g |
| Cetyl stearyl alcohol | 30 g |
| Sodium cetyl stearyl sulfate | 3 g |
| Solution of sodium bisulfite (35° Bé) | 1 cc |
| Ammonia (20% solution) | 20 cc |
| Water, q.s.p. | 100 g |

To 30 g of this composition there are added 90 g of hydrogen peroxide (30 volumes). The resulting mixture which is a cream having a pH of 9.5, is then applied to natural chestnut hair and is permitted to remain in contact therewith for 40 minutes. After rinsing and shampooing there is imparted to the hair a blond coloration, slightly ashen whereas with the same composition but without the diphenylamine there is obtained under the same conditions a blond coloration with golden glints.

EXAMPLE 11

The following dye composition is prepared:

| | |
|---|---|
| Paratolylenediamine | 0.6 g |
| 2-acetylamino-3,5-dimethyl-4,4'-dihydroxy diphenylamine hydrochloride | 0.2 g |
| 2-acetylamino-2',5-dimethyl-4-hydroxy-4'-N,N-(ethyl, carbamyl methyl) amino diphenylamine | 0.4 g |
| 2-amino-4-hydroxy-4'-N,N-(di-β-hydroxy ethyl) amino-5-methyl diphenylamine | 0.5 g |
| Nonyl phenol oxyethylenated with 4 moles of ethylene oxide (sold under the mark Remcopal 334) | 22 g |
| Nonyl phenol oxyethylenated with 9 moles of ethylene oxide (sold under the mark Remcopal 349) | 22 g |
| Butyl glycol | 8 g |
| Propylene glycol | 8 g |
| Solution of sodium bisulfite (35° Bé) | 1 g |
| Ammonia (22° Bé) | 12 cc |
| Water, q.s.p. | 100 g |

To 50 g of this composition there are added 50 g of hydrogen peroxide (20 volumes). The resulting mixture, which is a gel having a pH of 9.8, is then applied to the hair to be dyed. After rinsing and shampooing the following results are obtained:

(1) on natural blond hair and with a contact time of 30 minutes, a very pretty pearly ashen blond coloration is achieved;

(2) on deep natural blond hair with 80% white hair and with a contact time of 30 minutes, a deep ashen blond coloration, slightly moire, is achieved; and (3) with the same composition but without the diphenylamines and under the same conditions on the types of hair disclosed in (1) and (2), neutral colorations are achieved.

EXAMPLE 12

The following dye composition is prepared:

| | |
|---|---|
| Paratolylenediamine | 0.6 g |
| 2'-chloro-3,5-dimethyl-4,4'-dihydroxy diphenylamine hydrochloride | 0.2 g |
| 2-amino-3',5,5'-trimethyl-4,4'-dihydroxy diphenylamine | 0.4 g |
| 2-amino-3,5-dimethyl-4-hydroxy-4'-N,N-(di-β-hydroxyethyl) amino diphenylamine | 0.2 g |
| Nonyl phenol oxyethylenated with 4 moles of ethylene oxide (sold under the mark Remcopal 334) | 22 g |
| Nonyl phenol oxyethylenated with 9 moles of ethylene oxide (sold under the mark Remcopal 349) | 22 g |
| Butyl glycol | 8 g |
| Propylene glycol | 8 g |
| Solution of sodium bisulfite (35° Bé) | 1 g |
| Ammonia (22° Bé) | 12 cc |
| Water, q.s.p. | 100 g |

To 50 g of this composition there are added 50 g of hydrogen peroxide (20 volumes). The resulting mixture, which is a gel having a pH of 9.8, is then applied to the hair to be dyed. After rinsing and shampooing, the following results are obtained:

(1) on natural light blond hair and with a contact time of 30 minutes, a slightly pearly very luminous golden blond coloration is achieved;

(2) on natural blond hair and with a contact time of 30 minutes a golden blond coloration is obtained; and (3) with the same composition but without the diphenylamines, on the same types of hair in (1) and (2) and under the same conditions, neutral shades are achieved.

EXAMPLE 13

The following dye composition is prepared:

| | |
|---|---|
| Paratolylenediamine | 1 g |
| 2,5-dimethyl-4-hydroxy-4'-amino diphenylamine | 1 g |
| 2,4'-diamino-4-hydroxy-5-methyl diphenylamine dihydrochloride | 0.4 g |
| 2',6'-3,5-tetramethyl-4,4'-dihydroxy diphenylamine | 0.2 g |
| Nonyl phenol oxyethylenated with 4 moles of ethylene (sold under the mark Remcopal 334) | 15 g |
| Nonyl phenol oxyethylenated with 9 moles of ethylene oxide (sold under the mark Remcopal 349) | 12 g |
| Oleic acid | 3 g |
| Cetyl trimethyl ammonium bromide | 3 g |
| Copra diethanolamide | 7 g |
| Ethyl alcohol (96° titer) | 2 g |
| Butyl glycol | 5 g |
| Solution of sodium bisulfite (35° Bé) | 1 cc |
| Ammonia (22° Bé) | 8 cc |
| Water, q.s.p. | 100 g |

To 50 g of this composition there are added 50 g of hydrogen peroxide (20 volumes). The resulting mixture which is a gel having a pH of 9.8, is then applied to the hair to be dyed. After rinsing and shampooing, the following results are obtained:

(1) on natural deep blond hair and with a contact time of 30 minutes, a light chestnut coloration with pearly ashen glints is achieved;

(2) on natural chestnut hair with 80% white hair and with a contact time of 30 minutes, an iridescent maroon chestnut coloration which covers the white hair well is achieved; and (3) with the same composition but without the diphenylamines and under the same conditions on the types of hair disclosed in (1) and (2) there is imparted thereto similar colorations which are, however, less intense in glints and more yellow.

EXAMPLE 14

The following dye composition is prepared:

| | |
|---|---|
| Paratolylenediamine | 1 g |
| 2',3,5-trimethyl-4-hydroxy-4'-amino diphenylamine | 0.2 g |
| 2-carbamylmethyl amino-2',5-dimethyl-4-hydroxy-4-amino diphenylamine | 0.2 g |
| 2-acetylamino-2'-methoxy-4-hydroxy-4'-amino-5-methyl diphenylamine | 0.2 g |

| | | |
|---|---|---|
| 2-acetylamino-2'-methoxy-4-hydroxy-4'-amino-5,5'-dimethyl diphenylamine | 0.2 | g |
| 2-ureido-2'-chloro-4,4'-dihydroxy-5-methyl diphenylamine | 0.2 | g |
| Nonyl phenol oxyethylenated with 4 moles of ethylene oxide (sold under the mark Remcopal 334) | 15 | g |
| Nonyl phenol oxyethylenated with 9 moles of ethylene oxide (sold under the mark Remcopal 349) | 12 | g |
| Oleic acid | 3 | g |
| Cetyl trimethyl ammonium bromide | 3 | g |
| Copra diethanolamide | 7 | g |
| Ethyl alcohol (96° titer) | 2 | g |
| Butyl glycol | 5 | g |
| Solution of sodium bisulfite (35° Bé) | 1 | cc |
| Ammonia (22° Bé) | 8 | cc |
| Water, q.s.p. | 100 | g |

To 50 g of this composition there are added 50 g of hydrogen peroxide (20 volumes). The resulting mixture, which is a gel having a pH of 9.8, is then applied to the hair to be dyed. After rinsing and shampooing the following results are obtained:

(1) on light natural chestnut hair and with a contact time of 30 minutes, a golden maroon chestnut coloration is achieved;

(2) on natural chestnut hair and with a contact time of 30 minutes a very natural deep chestnut coloration is obtained; and (3) using the same composition but without the diphenylamines, under the same conditions and on the same types of hair in (1) and (2) above, similar colorations which are less intense and more neutral are attained.

EXAMPLE 15

The following dye composition is prepared:

| | | |
|---|---|---|
| Paratolylenediamine | 0.12 | g |
| Paraamino phenol | 0.25 | g |
| Resorcinol | 0.06 | g |
| Meta amino phenol | 0.06 | g |
| 2-acetylamino-2'-chloro-3,5-dimethyl-4,4'-dihydroxy diphenylamine | 0.4 | g |
| 2-amino-3,5-dimethyl-4-hydroxy-4'-N,N-(ethyl, β-sulfoethyl) amino diphenylamine | 0.2 | g |
| 2-acetylamino-3,5-dimethyl-3'-methoxy-4-hydroxy-4'-N-(β-hydroxyethyl) amino diphenylamine | 0.2 | g |
| Nonyl phenol oxyethylenated with 4 moles of ethylene oxide (sold under the mark Remcopal 334) | 22 | g |
| Nonyl phenol oxyethylenated with 9 moles of ethylene oxide (sold under the mark Remcopal 349) | 22 | g |
| Butyl glycol | 8 | g |
| Propylene glycol | 8 | g |
| Solution of sodium bisulfite (35° Bé) | 1 | g |
| Ammonia (22° Bé) | 12 | cc |
| Water, q.s.p. | 100 | g |

To 50 g of this composition there are added 50 g of hydrogen peroxide (20 volumes). The resulting mixture, which is a gel having a pH of 9.8, is then applied to the hair to be dyed. After rinsing and shampooing, the following results are obtained:

(1) on very light natural blond hair and with a contact time of 30 minutes, a golden beige light blond coloration is obtained;

(2) on bleached hair and with a contact time of 15 minutes, a pastel golden blond coloration is attained; and (3) using the same composition but without the diphenylamines, under the same conditions, and on the types of hair in (1) and (2) above, rather flat blond colorations were obtained.

EXAMPLE 16

The following dye composition is prepared:

| | | |
|---|---|---|
| Paratolylenediamine | 0.2 | g |
| Paraamino phenol | 0.3 | g |
| Meta diamino anisole sulfate | 0.2 | g |
| Resorcinol | 0.3 | g |
| Meta amino phenol | 0.1 | g |
| 2'-chloro-2,3-dimethyl-4,4'-dihydroxy diphenylamine | 0.3 | g |
| 2-acetylamino-2'-methoxy-4-hydroxy-4'-amino-5'-methyl diphenylamine | 0.3 | g |
| 2'-methoxy-3,3',5,5'-tetramethyl-4-hydroxy-4'-amino diphenylamine | 0.4 | g |
| 2,4'-diamino-5-methyl-4-hydroxy diphenylamine | 0.2 | g |
| Nonyl phenol oxyethylenated with 4 moles of ethylene oxide (sold under the mark Remcopal 334) | 15 | g |
| Nonyl phenol oxyethylenated with 9 moles of ethylene oxide (sold under the mark Remcopal 349) | 12 | g |
| Oleic acid | 3 | g |
| Cetyl trimethyl ammonium bromide | 3 | g |
| Copra diethanolamide | 7 | g |
| Ethyl alcohol (96° titer) | 2 | g |
| Butyl glycol | 5 | g |
| Solution of sodium bisulfite (35° Bé) | 1 | cc |
| Ammonia (22° Bé) | 12 | cc |
| Water, q.s.p. | 100 | g |

To 50 g of this composition there are added 50 g of hydrogen peroxide (20 volumes). The resulting mixture, which is a gel having a pH of 9.8, is then applied to the hair to be dyed. After rinsing and shampooing the following results are obtained:

(1) on deep natural blond hair with 80% white hair and with a contact time of 20 minutes, an iridescent maroon light chestnut coloration is obtained;

(2) on light natural chestnut hair and with a contact time of 20 minutes, a very luminous moire mahogany chestnut coloration is obtained;

(3) using the same composition but without the diphenylamines under the same conditions and on deep blond hair, a pearly ashen deep blond coloration is achieved; and (4) using the same composition but without the diphenylamines, under the same conditions and on light chestnut hair, a moire light maroon chestnut coloration is attained. Thus as can be noticed the compositions of the present invention provide a brightening of the color attained which exhibits warmer glints and is more luminous.

EXAMPLE 17

The following dye composition is prepared:

| | | |
|---|---|---|
| Paratolylenediamine | 0.2 | g |
| Para amino phenol | 0.3 | g |
| Meta diamino anisole sulfate | 0.2 | g |
| Resorcinol | 0.3 | g |
| Meta amino phenol | 0.1 | g |
| 3-methyl-4,6-diamino-4'-N,N-dimethylamino diphenylamine trihydrochloride | 0.1 | g |
| 2,4-diamino-5-methoxy-4'-N,N-(ethyl, carbamylmethyl) amino diphenylamine | 0.1 | g |
| Nonyl phenol oxyethylenated with 4 moles of ethylene oxide (sold under the mark Remcopal 334) | 15 | g |
| Nonyl phenol oxyethylenated with 9 moles of ethylene oxide (sold under the mark Remcopal 349) | 12 | g |
| Oleic acid | 3 | g |
| Cetyl trimethyl ammonium bromide | 3 | g |
| Copra diethanolamide | 7 | g |
| Ethyl alcohol (96°titer) | 2 | g |
| Butyl glycol | 5 | g |
| Solution of sodium bisulfite (35° Bé) | 1 | cc |
| Ammonia (22° Bé) | 12 | cc |
| Water, q.s.p. | 100 | g |

To 50 g of this composition there are added 50 g of hydrogen peroxide (20 volumes). The resulting mixture, which is a gel having a pH of 9.8, is then applied to deep natural blond hair and is permitted to remain in contact therewith for 30 minutes. After rinsing and shampooing a light chestnut coloration with ashen glints is obtained. When the same composition but without the diphenylamines is employed under the same conditions, a pearly ash blond coloration is obtained.

EXAMPLE 18

The following dye composition is prepared:

| | | |
|---|---|---|
| Paratolylenediamine | 0.5 | g |
| 2-acetylamino-3,3',5,5'-tetramethyl-4,4'-dihydroxy diphenylamine | 0.2 | g |
| 2',3,5,5'-tetramethyl-4-hydroxy-4'-amino diphenylamine | 0.2 | g |
| 4-hydroxy-4'-N,N-dimethyl amino diphenylamine | 0.2 | g |
| Cetyl stearyl alcohol | 20 | g |
| Sodium cetyl stearyl sulfate | 2 | g |
| Solution of sodium bisulfite (35° Bé) | 1 | cc |
| Ammonia (22° Bé) | 12 | cc |
| Water, q.s.p. | 100 | g |

To 50 g of this composition there are added 50 g of hydrogen peroxide (30 volumes). The resulting mixture, which is a cream having a pH of 9.6, is then applied to the hair to be dyed. After rinsing and shampooing, the following results are obtained:

(1) on deep natural blond hair with 80% white hair and with a contact time of 30 minutes, a blond coloration lightly ashen and which covers the white hair well is achieved;

(2) on light natural chestnut hair and with a contact time of 30 minutes, a natural very deep blond coloration is obtained; and (3) using the same composition but without the diphenylamines, under the same conditions and on the same types of hair as disclosed in (1) and (2) similar colorations but with reddish glints are obtained.

EXAMPLE 19

The following dye composition is prepared:

| | | |
|---|---|---|
| Paratolylenediamine | 0.5 | g |
| Resorcinol | 0.2 | g |
| 2-acetylamino-3',5,5'-trimethyl-4-hydroxy-4'-amino diphenylamine | 0.3 | g |
| 2'-chloro-2,3-dimethyl-4,4'-dihydroxy diphenylamine | 0.3 | g |
| Cetyl stearyl alcohol | 20 | g |
| Sodium cetyl stearyl sulfate | 2 | g |
| Solution of sodium bisulfite (35° Bé) | 1 | cc |
| Ammonia (22° Bé) | 12 | cc |
| Water, q.s.p. | 100 | g |

To 50 g of this composition there are added 100 g of hydrogen peroxide (20 volumes). The resulting mixture, which is a cream having a pH of 9.5, is then applied to light natural chestnut hair and is permitted to remain in contact therewith for 40 minutes. After rinsing and shampooing there is obtained a deep ash blond coloration. Using the same composition but without the diphenylamines and under the same conditions there is obtained a golden yellow deep blond coloration.

EXAMPLE 20

The following dye composition is prepared:

| | | |
|---|---|---|
| Paratolylenediamine | 1 | g |
| Resorcinol | 0.5 | g |
| 2-acetylamino-3,5-dimethyl-4-hydroxy-4'-N,N-(ethyl, carbamylmethyl) amino diphenylamine | 0.3 | g |
| 2-amino-4,4'-dihydroxy-5-methyl diphenylamine | 0.2 | g |
| Nonyl phenol oxyethylenated with 4 moles of ethylene oxide (sold under the mark Remcopal 334) | 15 | g |
| Nonyl phenol oxyethylenated with 9 moles of ethylene oxide (sold under the mark Remcopal 349) | 12 | g |
| Oleic acid | 3 | g |
| Cetyl trimethyl ammonium bromide | 3 | g |
| Copra diethanolamide | 7 | g |
| Ethyl alcohol (96° titer) | 2 | g |
| Butyl glycol | 5 | g |
| Solution of sodium bisulfite (35° Bé) | 1 | cc |
| Ammonia (22° Bé) | 12 | cc |
| Water, q.s.p. | 100 | g |

To 50 g of this composition there are added 50 g of hydrogen peroxide (20 volumes). The resulting mixture, which is a gel having a pH of 9.8, is then applied to natural blond hair having 80% white hair and is permitted to remain in contact therewith for 20 minutes. After rinsing and shampooing there is obtained a natural deep blond coloration. When using the same composition but without the diphenylamines, under the same conditions, there is obtained a deep blond coloration with flat yellow glints.

EXAMPLE 21

The following dye composition is prepared:

| | | |
|---|---|---|
| Paratolylenediamine | 0.6 | g |
| 3,5-dimethyl-4,4'-dihydroxy diphenylamine | 2 | g |
| Nonyl phenol oxyethylenated with 4 moles of ethylene oxide (sold under the mark Remcopal 334) | 22 | g |
| Nonyl phenol oxyethylenated with 9 moles of ethylene oxide (sold under the mark Remcopal 349) | 22 | g |
| Butyl glycol | 8 | g |
| Propylene glycol | 8 | g |
| Solution of sodium bisulfite (35° Bé) | 1 | g |
| Ammonia (22° Bé) | 10 | cc |
| Water, q.s.p. | 100 | g |

To 50 g of this composition there are added 50 g of hydrogen peroxide (20 volumes). The resulting mixture, which is a gel having a pH of 9.8, is then applied to deep natural blond hair having 80% white hair and is permitted to remain in contact therewith for 20 minutes. After rinsing and shampooing there is obtained a light blond coloration with pretty pearly golden glints. The color achieved is particularly luminous and the unison is excellent. When using the same composition but without the diphenylamine, under the same conditions, there is obtained a natural light blond coloration with very light warm ashen glints.

EXAMPLE 22

The following dye composition is prepared:

| | | |
|---|---|---|
| Paratolylenediamine | 0.6 | g |
| 3,5-dimethyl-4,4'-dihydroxy diphenylamine | 2 | g |
| 2-amino-4,4'-dihydroxy-5-methyl diphenylamine | 1 | g |
| Nonyl phenol oxyethylenated with 4 moles of ethylene oxide (sold under the mark Remcopal 334) | 22 | g |
| Nonyl phenol oxyethylenated with 9 moles of ethylene oxide (sold under the mark Remcopal 349) | 22 | g |
| Butyl glycol | 8 | g |
| Solution of sodium bisulfite (35° Bé) | 1 | g |
| Ammonia (22° Bé) | 10 | cc |
| Water, q.s.p. | 100 | g |

To 50 g of this composition there are added 50 g of hydrogen peroxide (20 volumes). The resulting mixture, which is a gel having a pH of 9.8, is then applied to deep natural blond hair having 80% white hair and is permitted to remain in contact therewith for 20 minutes. After rinsing and shampooing there is obtained a light blond coloration with pretty golden copper glints. The color obtained is particularly luminous and the unison is excellent. When using the same composition but without the diphenylamines, under the same conditions there is obtained a natural light blond color with very light warm ashen glints.

EXAMPLE 23

The following dye composition is prepared:

| | | |
|---|---|---|
| Paratolylenediamine | 0.6 | g |
| 2-amino-4,4'-dihydroxy-5-methyl diphenylamine | 1 | g |
| 2,4-diamino-5-methoxy-4'-hydroxy diphenylamine dihydrochloride | 0.5 | g |
| Nonyl phenol oxyethylenated with 4 moles of ethylene oxide (sold under the mark Remcopal 334) | 22 | g |
| Nonyl phenol oxyethylenated with 9 moles of ethylene oxide (sold under the mark Remcopal 349) | 22 | g |
| Butyl glycol | 8 | g |
| Propylene glycol | 8 | g |
| Solution of sodium bisulfite (35° Bé) | 1 | g |
| Ammonia (22° Bé) | 10 | cc |
| Water, q.s.p. | 100 | g |

To 50 g of this composition there are added 50 g of hydrogen peroxide (20 volumes). The resulting mixture, which is a gel having a pH of 9.8, is then applied to deep natural blond hair having 80% white hair and is permitted to remain in contact therewith for 20 minutes. After rinsing and shampooing, there is obtained a blond color with deep copper mahogany glints. The color is particularly luminous and the unison is excellent. When using the same composition but without the diphenylamines, under the same conditions, a natural light blond color with very light warm ashen glints is obtained.

EXAMPLE 24

The following dye composition is prepared:

| | | |
|---|---|---|
| Paratolylenediamine | 0.6 | g |
| 3,5-dimethyl-4-hydroxy-4'-amino diphenylamine | 0.5 | g |
| Nonyl phenol oxyethylenated with 4 moles of ethylene oxide (sold under the mark Remcopal 334) | 22 | g |
| Nonyl phenol oxyethylenated with 9 moles of ethylene oxide (sold under the mark Remcopal 349) | 22 | g |
| Butyl glycol | 8 | g |
| Propylene glycol | 8 | g |
| Solution of sodium bisulfite (35° Bé) | 1 | g |
| Ammonia (22° Bé) | 10 | cc |
| Water, q.s.p. | 100 | g |

To 50 g of this composition there are added 50 g of hydrogen peroxide (20 volumes). The resulting mixture, which is a gel having a pH of 9.8 is then applied to deep natural blond hair having 80% white hair and is permitted to remain in contact therewith for 20 minutes. After rinsing and shampooing, a light blond color with pearly ashen glints is obtained. The color is particularly luminous and the unison is excellent. When using the same composition but without the diphenylamine, under the same conditions, a natural light blond color with very light warm ashen glints is obtained.

EXAMPLE 25

The following dye composition is prepared:

| | | |
|---|---|---|
| Paratolylenediamine | 0.12 | g |
| Resorcinol | 0.06 | g |

| | | |
|---|---|---|
| Meta amino phenol | 0.064 | g |
| Para amino phenol | 0.23 | g |
| 2-amino-4,4'-dihydroxy-5-methyl diphenylamine | 0.18 | g |
| 3,5-dimethyl-4,4'-dihydroxy diphenylamine | 0.18 | g |
| Nonyl phenol oxyethylenated with 4 moles of ethylene oxide (sold under the mark Remcopal 334) | 22 | g |
| Nonyl phenol oxyethylenated with 9 moles of ethylene oxide (sold under the mark Remcopal 349) | 22 | g |
| Butyl glycol | 8 | g |
| Propylene glycol | 8 | g |
| Solution of sodium bisulfite (35° Bé) | 1 | g |
| Ammonia (22° Bé) | 12 | cc |
| Water, q.s.p. | 100 | g |

To 50 g of this composition there are added 50 g of hydrogen peroxide (20 volumes). The resulting mixture, which is a gel having a pH of 9.8, is then applied to deep natural blond hair and is permitted to remain in contact therewith for 20 minutes. After rinsing and shampooing there is obtained a very pretty golden light blond color which is particularly luminous and exhibits very good unison. When using the same composition but without the diphenylamines under the same conditions, a very neutral natural light blond color is obtained.

EXAMPLE 26

The following dye composition is prepared:

| | | |
|---|---|---|
| Paratolylenediamine | 0.035 | g |
| Meta diamino anisol sulfate | 0.015 | g |
| Meta amino phenol | 0.015 | g |
| Para amino phenol | 0.5 | g |
| 2,4-diamino-5-methoxy-4'-hydroxy diphenylamine dihydrochloride | 0.60 | g |
| Nitro paraphenylene diamine | 0.15 | g |
| 2-amino-4,4'-dihydroxy-5-methyl diphenylamine | 0.80 | g |
| Nonyl phenol oxyethylenated with 4 moles of ethylene oxide (sold under the mark Remcopal 334) | 22 | g |
| Nonyl phenol oxyethylenated with 9 moles of ethylene oxide (sold under the mark Remcopal 349) | 22 | g |
| Butyl glycol | 8 | g |
| Propylene glycol | 8 | g |
| Solution of sodium bisulfite (35° Bé) | 1 | g |
| Ammonia (22° Bé) | 12 | cc |
| Water, q.s.p. | 100 | g |

To 50 g of this composition there are added 50 g of hydrogen peroxide (20 volumes). The resulting mixture, which is a gel having a pH of 9.8, is then applied to deep natural blond hair having 80% white hair and is permitted to remain in contact therewith for 20 minutes. After rinsing and shampooing a light blond color with rather intense copper mahogany glints is obtained. When using the same composition but without the diphenylamines, under the same conditions a light blond color with much lighter pink copper glints is obtained. The color obtained with the diphenylamine-containing composition is much more luminous and exhibits better unison than that obtained with the diphenylamine-free composition.

EXAMPLE 27

The following dye composition is prepared:

| | | |
|---|---|---|
| Paratolylenediamine | 1 | g |
| 2-amino-3,5-dimethyl-4,4'-dihydroxy diphenylamine | 1.6 | g |
| 3,3',5,5'-tetramethyl-4-hydroxy-4'-amino diphenylamine | 0.6 | g |
| Nonyl phenol oxyethylenated with 4 moles of ethylene oxide (sold under the mark Remcopal 334) | 15 | g |
| Nonyl phenol oxyethylenated with 9 moles of ethylene oxide (sold under the mark Remcopal 349) | 12 | g |
| Oleic acid | 3 | g |
| Cetyl trimethyl ammonium bromide | 3 | g |
| Copra diethanolamide | 7 | g |
| Ethyl alcohol (96° titer) | 8 | g |
| Propylene glycol | 2 | g |
| Butyl glycol | 5 | g |
| Solution of sodium bisulfite (350° Bé) | 1 | cc |
| Ammonia (22° Bé) | 12 | cc |
| Water, q.s.p. | 100 | g |

To 50 g of this composition there are added 50 g of hydrogen peroxide (20 volumes). The resulting mixture, which is a gel having a pH of 9.8 is then applied to the hair to be dyed. After rinsing and shampooing the following results are obtained:

(1) on very light (bleached) blond hair and with a contact time of 30 minutes, a light blond color with coppery mahogany glints is obtained;

(2) on natural blond hair and with a contact time of 30 minutes, a blond color with coppery ashen glints is achieved;

(3) on light natural chestnut hair and with a contact time of 30 minutes, a deep blond color with coppery ashen glints is obtained;

(4) on natural chestnut hair and with a contact time of 30 minutes, a light chestnut color with coppery mahogany glints is attained; and (5) with the same composition but without the diphenylamine and on the same types of hair disclosed in (1) to (4) and under the same conditions, similar colors are achieved but they have less intense glints and are more yellow.

EXAMPLE 28

The following dye composition is prepared:

| | | |
|---|---|---|
| Paratolylenediamine | 1 | g |
| 2-ureido-4-hydroxy-4'-amino diphenylamine | 0.5 | g |
| 2-amino-4,4'-dihydroxy-5-methyl diphenylamine | 0.4 | g |
| 2,4'-diamino-3,5-dimethyl-4-hydroxy diphenylamine | 1 | g |
| Nonyl phenol oxyethylenated with 4 moles of ethylene oxide (sold under the mark Remcopal 334) | 15 | g |
| Nonyl phenol oxyethylenated with 9 moles of ethylene oxide (sold under the mark Remcopal 349) | 12 | g |
| Oleic acid | 3 | g |
| Cetyl trimethyl ammonium bromide | 3 | g |

-continued

| | | |
|---|---|---|
| Copra diethanolamide | 7 | g |
| Ethyl alcohol (96° titer) | 8 | g |
| Propylene glycol | 2 | g |
| Butyl glycol | 5 | g |
| Solution of sodium bisulfite (35° Bé) | 1 | cc |
| Ammonia (22° Bé) | 12 | cc |
| Water, q.s.p. | 100 | g |

To 50 g of this composition there are added 50 g of hydrogen peroxide (20 volumes). The resulting mixture which is a gel having a pH of 9.8 is then applied to the hair to be dyed. After rinsing and shampooing, the following results are obtained:

(1) on very light (bleached) blond hair and with a contact time of 15 minutes, an intense purple violet color is obtained;

(2) on natural blond hair and with a contact time of 15 minutes, a moire mahogany blond color is achieved;

(3) on natural blond hair and with a contact time of 30 minutes, a deep violet mahogany blond color is obtained;

(4) on light natural chestnut hair and with a contact time of 30 minutes, an iridescent maroon light chestnut color is attained;

(5) on natural chestnut hair and with a contact time of 30 minutes, a moire mahogany chestnut color is obtained; and (6) using the same compositions but without the diphenylamines, on the types of hair disclosed in (1)-(5) and under the same conditions similar colors are obtained but they have less intense glints.

EXAMPLE 29

The following dye composition is prepared:

| | | |
|---|---|---|
| Paratolylenediamine | 0.2 | g |
| Para amino phenol | 0.3 | g |
| Meta diamino anisole sulfate | 0.2 | g |
| Resorcinol | 0.3 | g |
| Meta amino phenol | 0.1 | g |
| 2-amino-4,4'-dihydroxy-5-methyl diphenylamine | 0.4 | g |
| 2,4-diamino-5-methoxy-4'-hydroxy diphenylamine dihydrochloride | 0.2 | g |
| 3,5-dimethyl-4-hydroxy-4'-amino diphenylamine | 0.1 | g |
| Nonyl phenol oxyethylenated with 4 moles of ethylene oxide (sold under the mark Remcopal 334) | 15 | g |
| Nonyl phenol oxyethylenated with 9 moles of ethylene oxide (sold under the mark Remcopal 349) | 12 | g |
| Oleic acid | 3 | g |
| Cetyl trimethylammonium bromide | 3 | g |
| Copra diethanolamide | 7 | g |
| Ethyl alcohol (96° titer) | 8 | g |
| Propylene glycol | 2 | g |
| Butyl glycol | 5 | g |
| Solution of sodium bisulfite (35° Bé) | 1 | cc |
| Ammonia (22° Bé) | 12 | cc |
| Water, q.s.p. | 100 | g |

To 50 g of this composition there are added 50 g of hydrogen peroxide (20 volumes). The resulting mixture, which is a gel having a pH of 9.8, is then applied to the hair to be dyed. After rinsing and shampooing, the following results are obtained:

(1) on deep natural blond hair and with a contact time of 30 minutes, a light chestnut color with purplish mahogany glints is obtained;

(2) on natural chestnut hair and with a contact time of 30 minutes, a deep mahogany chestnut color is obtained;

(3) using the same composition but without the diphenylamines and under the same conditions, on deep natural blond hair, an iridescent deep blond color is achieved; and (4) using the same composition but without the diphenylamines and under the same conditions, on natural chestnut hair, an iridescent maroon chestnut color is attained.

EXAMPLE 30

The following dye composition is prepared:

| | | |
|---|---|---|
| Paratolylenediamine | 0.6 | g |
| 3,5-dimethyl-4,4'-dihydroxy diphenylamine | 2 | g |
| 2'-methoxy-2,3',5,5'-tetramethyl-4-hydroxy-4'-amino diphenylamine | 0.5 | g |
| Nonyl phenol oxyethylenated with 4 moles of ethylene oxide (sold under the mark Remcopal 334) | 15 | g |
| Nonyl phenol oxyethylenated with 9 moles of ethylene oxide (sold under the mark Remcopal 349) | 10 | g |
| Oleic acid | 15 | g |
| Ethyl alcohol (96° titer) | 10 | g |
| Propylene glycol | 15 | g |
| Solution of sodium bisulfite (35° Bé) | 1 | cc |
| Ammonia (22° Bé) | 15 | cc |
| Water, q.s.p. | 100 | g |

To 50 g of this composition there are added 50 g of hydrogen peroxide (20 volumes). The resulting mixture, which is a gel having a pH of 9.4, is then applied to the hair to be dyed. After rinsing and shampooing the following results are obtained:

(1) on bleached hair (deep light yellow) and with a contact time of 5 minutes, a pastel golden beige color is obtained;

(2) on bleached hair and with a contact time of 30 minutes, a beige light blond color with copper glints is obtained;

(3) on deep natural blond hair and with a contact time of 30 minutes a blond color with golden glints is achieved; and (4) using the same composition but without the diphenylamines, under the same conditions, a natural blond color is obtained.

EXAMPLE 31

The following dye composition is prepared:

| | | |
|---|---|---|
| Paratolylenediamine | 0.3 | g |
| Para amino phenol | 0.2 | g |
| Resorcinol | 0.2 | g |
| Meta amino phenol | 0.1 | g |
| 2-acetylamino-4-hydroxy-4'-amino-5-methyl diphenylamine | 0.8 | g |
| 2'-methoxy-3,5-dimethyl-4-hydroxy-4'-amino diphenylamine | 0.5 | g |
| Nonyl phenol oxyethylenated with 4 moles of ethylene oxide (sold under the mark Remcopal 334) | 15 | g |

| | | |
|---|---|---|
| Nonyl phenol oxyethylenated with 9 moles of ethylene oxide (sold under the mark Remcopal 349) | 10 | g |
| Oleic acid | 15 | g |
| Ethyl alcohol (96° titer) | 10 | g |
| Propylene glycol | 15 | g |
| Solution of sodium bisulfite (35° Bé) | 1 | cc |
| Ammonia (22° Bé) | 15 | cc |
| Water, q.s.p. | 100 | g |

To 50 g of this composition there are added 50 g of hydrogen peroxide (20 volumes). The resulting mixture which is a gel having a pH of 9.8 is then applied to the hair to be dyed. After rinsing and shampooing, the following results are obtained:

(1) on deep natural blond hair having 80% white hair and with a contact time of 30 minutes, a deep blond color with bluish ashen glints is obtained, (2) on natural blond hair and with a contact time of 30 minutes, a light ash chestnut color is achieved;

(3) on light natural chestnut hair and with a contact time of 30 minutes, a luminous natural chestnut color is attained;

(4) with the same composition but without the diphenylamines, under the same conditions and on deep natural blond hair with 80% white hair, a light ash blond color is obtained; and (5) with the same composition but without the diphenylamines, under the same conditions and on natural blond hair, a slightly ashen blond color is obtained.

EXAMPLE 32

The following dye composition is prepared:

| | | |
|---|---|---|
| Paratolylenediamine | 1 | g |
| 2-ureido-4-hydroxy-4'-amino diphenylamine | 0.5 | g |
| 3,3',5,5'-tetramethyl-4-hydroxy-4'-amino diphenylamine | 0.4 | g |
| Cetyl stearyl alcohol | 20 | g |
| Sodium cetyl stearyl sulfate | 2 | g |
| Sodium bisulfite solution (35° Bé) | 1 | cc |
| Ammonia (20% solution) | 12 | cc |
| Water, q.s.p. | 100 | g |

To 50 g of this composition there are added 50 g of hydrogen peroxide (20 volumes). The resulting mixture, which is a cream having a pH of 9.8, is then applied to the hair to be dyed. After rinsing and shampooing, the following results are obtained:

(1) on deep natural blond hair with 80% white hair and a contact time of 20 minutes, an iridescent maroon chestnut color is obtained;

(2) on natural chestnut hair with 80% white hair and a contact time of 20 minutes, a deep chestnut color is achieved;

(3) using the same composition but without the diphenylamines, under the same conditions and on deep natural blond hair with 80% white hair, a deep golden blond color is obtained; and (4) using the same composition but without the diphenylamines, under the same conditions and on natural chestnut hair with 80% white hair, a chestnut color with golden coppery glints is achieved.

EXAMPLE 33

The following dye composition is prepared:

| | | |
|---|---|---|
| Paratolylenediamine | 0.1 | g |
| Resorcinol | 0.1 | g |
| 3,5-dimethyl-4-hydroxy-4'-amino diphenylamine | 0.4 | g |
| Cetyl stearyl alcohol | 30 | g |
| Sodium cetyl stearyl sulfate | 3 | g |
| Ethyl alcohol (96° titer) | 1 | g |
| Solution of sodium bisulfite (35° Bé) | 1 | cc |
| Ammonia (20% solution) | 20 | cc |
| Water, q.s.p. | 100 | g |

To 30 g of this composition there are added 90 g of hydrogen peroxide (30 volumes). The resulting mixture, which is a cream having a pH of 9.8, is then applied to natural light chestnut hair and is permitted to remain in contact therewith for 40 minutes. After rinsing and shampooing, a very pretty pearly beige blond color is obtained.

EXAMPLE 34

The following dye composition is prepared:

| | | |
|---|---|---|
| Paratolylenediamine | 0.15 | g |
| Para amino phenol | 0.5 | g |
| Meta diamino anisole sulfate | 0.03 | g |
| Resorcinol | 0.1 | g |
| Meta amino phenol | 0.08 | g |
| 3-N-[(4'-hydroxy)phenyl]amino-6-methyl benzoquinone-imine | 0.12 | g |
| 2,4-diamino-5-methoxy-4'-hydroxy diphenylamine dihydrochloride | 0.08 | g |
| Nonyl phenol oxyethylenated with 4 moles of ethylene oxide (sold under the mark Remcopal 334) | 15 | g |
| Nonyl phenol oxyethylenated with 9 moles of ethylene oxide (sold under the mark Remcopal 349) | 12 | g |
| Oleic acid | 3 | g |
| Cetyl trimethyl ammonium bromide | 3 | g |
| Copra diethanolamide | 7 | g |
| Ethyl alcohol (96° titer) | 8 | g |
| Propylene glycol | 2 | g |
| Butyl glycol | 5 | g |
| Solution of sodium bisulfite (35° Bé) | 1 | cc |
| Ammonia (22° Bé) | 12 | cc |
| Water, q.s.p. | 100 | g |

To 50 g of this composition there are added 50 g of water containing 1 g % of ammonium persulfate, the mixture being prepared just before the use thereof, and being a gel having a pH of 10. The gel is then applied to the hair to be dyed and after rinsing and shampooing the following results are obtained:

(1) on bleached hair (deep light yellow) and with a contact time of 5 minutes, a very pretty very light beige golden blond color is obtained; and (2) on deep natural blond hair and with a contact time of 20 minutes, a very distinct shading is obtained, the color becoming deep blond with ashen mahogany glints.

To 50 g of this same composition there are added 50 g of hydrogen peroxide (20 volumes). The resulting mixture which is a gel having a pH of 9.8 is then applied to the hair to be dyed. After rinsing and shampooing the following results are obtained:

(1) on deep natural blond hair and with a contact time of 30 minutes, a blond color with very luminous golden mahogany glints is obtained; and (2) on natural light chestnut hair and with a contact time of 30 minutes, a deep blond color with coppery mahogany glints is achieved.

EXAMPLE 35

The following dye composition is prepared:

| | | |
|---|---|---|
| Paratolylenediamine | 0.6 | g |
| 2-acetylamino-3'-chloro-4-hydroxy-4'-N-(ethyl) amino-5-methyl diphenylamine | 0.3 | g |
| 2-acetylamino-3,3',5-trimethyl-4-hydroxy-4'-N-(mesyl-aminoethyl)amino diphenylamine | 0.2 | g |
| Nonyl phenol oxyethylenated with 4 moles of ethylene oxide (sold under the mark Remcopal 334) | 22 | g |
| Nonyl phenol oxyethylenated with 9 moles of ethylene oxide (sold under the mark Remcopal 349) | 22 | g |
| Butyl glycol | 8 | g |
| Propylene glycol | 8 | g |
| Solution of sodium bisulfite (35° Bé) | 1 | g |
| Ammonia (22° Bé) | 12 | cc |
| Water, q.s.p. | 100 | g |

To 50 g of this composition there are added 50 g of hydrogen peroxide (20 volumes). The resulting mixture, which is a gel having a pH of 9.8, is then applied to the hair to be dyed. After rinsing and shampooing the following results are obtained:

(1) on bleached hair and with a contact time of 5 minutes, a very light ash blond color is obtained;

(2) on deep natural blond hair having 80% white hair and with a contact time of 30 minutes, an ash blond color is achieved; and (3) using the same composition but without the diphenylamines, under the same conditions, neutral colors without glints are obtained.

EXAMPLE 36

The following hair dye composition is prepared:

| | | |
|---|---|---|
| Chloro-paraphenylenediamine sulfate | 0.8 | g |
| 3-chloro-4-amino phenol hydrochloride | 0.4 | g |
| 5-ureido-2-methyl phenol | 0.2 | g |
| 2,6-dimethyl-5-amino phenol | 0.1 | g |
| Picramic acid | 0.12 | g |
| 2-carbamylmethylamino-4-hydroxy-4'-N,N-(ethyl, β-mesylaminoethyl) amino-5-methyl) diphenylamine | 0.04 | g |
| 2-hydroxyethylamino-2'-chloro-4,4'-dihydroxy-5-methyl diphenylamine | 0.26 | g |
| Sodium lauryl sulfate oxyethylenated with 2 moles of ethylene oxide | 20 | g |
| Copra diethanolamide | 3 | g |
| Derivative of meta acrylic acid (sold under the mark "Carbopol") | 1 | g |
| Ethyl glycol | 5 | g |
| Monoethanolamine | 4 | g |

| -continued | | |
|---|---|---|
| Water, q.s.p. | 100 | g |

To 50 g of this composition there are added 50 g of urea peroxide at the moment of use. The resulting mixture which is a thickened foamy liquid having a pH of 10 is applied, immediately after preparation of the same, to deep natural blond hair and is permitted to remain in contact therewith for 15 minutes. After rinsing and shampooing, a pretty golden light maroon color is obtained.

EXAMPLE 37

The following dye composition is prepared:

| | | |
|---|---|---|
| 2,6-dimethyl paraphenylenediamine dihydrochloride | 1 | g |
| 2,6-dimethyl-4-amino phenol | 0.6 | g |
| 2,6-dimethyl-5-acetylamino phenol | 0.4 | g |
| Resorcinol | 0.5 | g |
| 2-hydroxyethylamino-3'-chloro-4,4'-dihydroxy-5-methyl diphenylamine | 0.4 | g |
| 3,5-dimethyl-3'-chloro-4-hydroxy-4'-dimethylamino diphenylamine | 0.08 | g |
| 2-β-aminoethyl amino anthraquinone hydrochloride | 0.1 | g |
| Nonyl phenol oxyethylenated with 4 moles of ethylene oxide (sold under the mark Remcopal 334) | 15 | g |
| Nonyl phenol oxyethylenated with 9 moles of ethylene oxide (sold under the mark Remcopal 349) | 12 | g |
| Oleic acid | 3 | g |
| Cetyl trimethyl ammonium bromide | 3 | g |
| Copra diethanolamide | 7 | g |
| Ethyl alcohol (96° titer) | 8 | g |
| Propylene glycol | 5 | g |
| Sodium bisulfite (35° Bé) | 1 | cc |
| Ammonia (22° Bé) | 15 | cc |
| Water, q.s.p. | 100 | g |

To 50 g of this composition there are added 50 g of hydrogen peroxide (20 volumes). The resulting mixture which has a pH of 9.4 is then applied to the hair to be dyed. After rinsing and shampooing, the following results are obtained:

(1) on bleached hair and with a contact time of 5 minutes, a golden beige color is obtained; and (2) on deep natural blond hair and with a contact time of 20 minutes, a pearly golden deep blond color is obtained.

EXAMPLE 38

The following dye composition is prepared:

| | | |
|---|---|---|
| 2,6-dimethyl-5-methoxy paraphenylenediamine dihydrochloride | 0.3 | g |
| Para amino phenol | 0.4 | g |
| 2-methyl-5-acetylamino phenol | 0.2 | g |
| Resorcinol | 0.2 | g |
| 2-acetylamino-3',5-dimethyl-4-hydroxy-4'-N-ethylamino diphenylamine | 0.3 | g |
| 2-hydroxyethylamino-4,4'-dihydroxy-5-methyl diphenylamine | 0.3 | g |
| 3,5-dimethyl-4,4'-dihydroxy | | |

| | | |
|---|---|---|
| -continued | | |
| diphenylamine | 0.2 | g |
| Cetyl stearyl alcohol | 20 | g |
| Sodium cetyl stearyl sulfate | 2 | g |
| Sodium bisulfite (35° Bé) | 1 | cc |
| Ammonia (20% solution) | 15 | cc |
| Water, q.s.p. | 100 | g |

To 30 g of this composition in the form of a cream there are added 60 g of hydrogen peroxide (20 volumes). The resulting mixture is then applied to light natural chestnut hair having 80% white hair and is permitted to remain in contact therewith for 20 minutes. After rinsing and shampooing a pearly golden blond color is obtained.

EXAMPLE 39

The following dye composition is prepared:

| | | |
|---|---|---|
| 2-methyl-5-methoxy paraphenylene-diamine dihydrochloride | 0.1 | g |
| 4-amino-N,N-(ethyl, piperidinoethyl) aniline trihydrochloride | 0.2 | g |
| 3-chloro-4-amino phenol hydrochloride | 0.1 | g |
| 2,6-dimethyl-5-acetylamino phenol | 0.06 | g |
| 2,6-dimethyl-5-amino phenol | 0.1 | g |
| 2-methoxy-4-hydroxy-4'-N,N-dimethyl-amino diphenylamine | 0.08 | g |
| 4-methoxy-N-($\beta$-hydroxyethyl) orthonitroaniline | 0.04 | g |
| Sodium lauryl sulfate oxyethylenated with 2 moles of ethylene oxide | 20 | g |
| Copra diethanolamide | 3 | g |
| Derivative of meta acrylic acid (sold under the mark "Carbopol") | 1 | g |
| Ethyl glycol | 5 | g |
| Monoethanolamine | 2 | g |
| Water, q.s.p. | 100 | g |

To 50 g of this composition there is added at the moment of use 0.2 g of sodium persulfate. The resulting mixture, which is a thickened foamy liquid having a pH of 9 is applied immediately after preparation of the same to moist or wet bleached hair and is permitted to remain in contact therewith for 15 minutes. After rinsing and shampooing a very pretty pearly beige color is obtained.

To 50 g of this composition there are added 5 g of urea peroxide and the resulting mixture is applied immediately after preparation of the same to moist or wet deep natural blond hair and is permitted to remain in contact therewith for 30 minutes. After rinsing and shampooing a blond color with iridescent glints is obtained.

EXAMPLE 40

The following dye composition is prepared:

| | | |
|---|---|---|
| 3-methyl-4-amino-N-methyl aniline dihydrochloride | 0.4 | g |
| 2-chloro-4-amino-N,N-(ethyl, sulfonamido ethyl) aniline sulfate | 0.1 | g |
| Meta diamino anisole sulfate | 0.06 | g |
| Meta amino phenol | 0.1 | g |
| 2-hydroxyethylamino-4,4'-dihydroxy-5-methyl | | |
| diphenylamine | 0.14 | g |
| 2-amino-2'-methoxy-3,5-dimethyl-4-hydroxy-4'-N,N-dimethylamino diphenylamine | 0.08 | g |
| Nonyl phenol oxyethylenated with 4 moles of ethylene oxide (sold under the mark Remcopal 334) | 22 | g |
| Nonyl phenol oxyethylenated with 9 moles of ethylene oxide (sold under the mark Remcopal 349) | 22 | g |
| Butyl glycol | 8 | g |
| Propylene glycol | 8 | g |
| Solution of sodium bisulfite (35° Bé) | 1 | cc |
| Ammonia (22° Bé) | 10 | cc |
| Water, q.s.p. | 100 | g |

To 50 g of this composition there are added 50 g of hydrogen peroxide (20 volumes). The resulting mixture is then applied to moist light natural chestnut hair and is permitted to remain in contact therewith for 30 minutes. After rinsing and shampooing a deep ash blond coloration is obtained.

EXAMPLE 41

The following dye composition is prepared:

| | | |
|---|---|---|
| 3-methyl-4-amino-N,N-(ethyl, $\beta$-mesylamino-ethyl) aniline sulfate | 0.2 | g |
| 4-amino-N,N-(ethyl, carbamylmethyl) aniline | 0.1 | g |
| Para amino phenol | 0.1 | g |
| Diamino anisole sulfate | 0.02 | g |
| Resorcinol | 0.16 | g |
| Meta amino phenol | 0.1 | g |
| 2-acetylamino-2',3,5-trimethyl-4-hydroxy-4'-N,N-(ethyl, $\beta$-mesylaminoethyl) amino diphenylamine | 0.06 | g |
| 2-acetylamino-2',5-dimethyl-4-hydroxy-4'-N,N-(ethyl, carbamylmethyl) amino diphenylamine | 0.1 | g |
| Cetyl stearyl alcohol | 20 | g |
| Sodium cetyl stearyl sulfate | 2 | g |
| Solution of sodium bisulfite (35° Bé) | 1.4 | cc |
| Ammonia (20% solution) | 2 | cc |
| Water, q.s.p. | 100 | g |

To 30 g of this creamy composition there are added 60 g of hydrogen peroxide (20 volumes). The resulting mixture, which has a pH of 9 is then applied to dry hair having 80% white hair and is permitted to remain in contact therewith for 20 minutes. After rinsing and shampooing, a bluish gray color is obtained.

EXAMPLE 42

The following dye composition is prepared:

| | | |
|---|---|---|
| 2-chloro-4-amino-N-(ethyl) aniline sulfate | 0.22 | g |
| 2-methyl-4-amino-N-($\beta$-hydroxyethyl) aniline sulfate | 0.08 | g |
| 3-chloro-4-amino phenol hydrochloride | 0.1 | g |
| 2,6-dimethyl-5-acetylamino phenol | 0.1 | g |
| 2,6-dimethyl-5-amino phenol | 0.1 | g |
| 2,4'-diamino-3-methyl-4-hydroxy diphenylamine | 0.16 | g |

| | | |
|---|---|---|
| 4-methoxy-N-(β-hydroxyethyl) orthonitroaniline | 0.1 | g |
| Nonyl phenol oxyethylenated with 4 moles of ethylene oxide (sold under the mark Remcopal 334) | 15 | g |
| Nonyl phenol oxyethylenated with 9 moles of ethylene oxide (sold under the mark Remcopal 349) | 12 | g |
| Oleic acid | 3 | g |
| Cetyl trimethyl ammonium bromide | 3 | g |
| Copra diethanolamide | 7 | g |
| Ethyl alcohol (96° titer) | 8 | g |
| Propylene glycol | 2 | g |
| Butyl glycol | 5 | g |
| Solution of sodium bisulfite (35° Bé) | 1 | cc |
| Ammonia (20% solution) | 10 | cc |
| Water, q.s.p. | 100 | g |

To 50 g of this composition there are added 50 g of hydrogen peroxide (20 volumes). The resulting mixture, which is a gel, is then applied to wet, dull deep natural blond hair and is permitted to remain in contact therewith for 30 minutes. After rinsing and shampooing, a moire mahogany blond color is obtained.

EXAMPLE 43

The following dye composition is prepared:

| | | |
|---|---|---|
| 3-methyl-4-amino-N,N-(ethyl, β-سulfoethyl) aniline | 0.4 | g |
| 4-amino-N,N-(ethyl, β-sulfoethyl) aniline | 0.2 | g |
| 3-methyl-4-amino-N,N-(ethyl, carbamylmethyl) aniline | 0.1 | g |
| Resorcinol | 0.2 | g |
| Meta amino phenol | 0.1 | g |
| 2-acetylamino-2',5-dimethyl-4-hydroxy-4'-N,N-(ethyl, β-mesylaminoethyl) amino diphenylamine | 0.06 | g |
| 2-amino-2'-chloro-4,4'-dihydroxy-5-methyl diphenylamine | 0.08 | g |
| Nonyl phenol oxyethylenated with 4 moles of ethylene oxide (sold under the mark Remcopal 334) | 22 | g |
| Nonyl phenol oxyethylenated with 9 moles of ethylene oxide (sold under the mark Remcopal 349) | 22 | g |
| Butyl glycol | 8 | g |
| Propylene glycol | 8 | g |
| Solution of sodium bisulfite (35° Bé) | 1 | cc |
| Ammonia (22° Bé) | 10 | cc |
| Water, q.s.p. | 100 | g |

To 50 g of this composition there are added 50 g of hydrogen peroxide (20 volumes). The resulting mixture is then applied to wet, dull natural blond hair and is permitted to remain in contact therewith for 30 minutes. After rinsing and shampooing a light ash blond color is obtained.

EXAMPLE 44

The following dye composition is prepared:

| | | |
|---|---|---|
| 4-amino-N,N-(ethyl, acetylaminoethyl) aniline semi-sulfate | 0.4 | g |
| 4-amino-2-methoxy-N-(β-hydroxyethyl) aniline | 0.2 | g |
| Para amino phenol | 0.4 | g |
| Meta diamino anisole sulfate | 0.02 | g |
| Resorcinol | 0.3 | g |
| 2-ureido-2',5-dimethyl-4-hydroxy-4'-N,N-(ethyl, carbamylmethyl) amino diphenylamine | 0.08 | g |
| 2-acetylamino-3,5-dimethyl-3'-chloro-4-hydroxy-4'-N,N-dimethyl diphenylamine | 0.06 | g |
| Nonyl phenol oxyethylenated with 4 moles of ethylene oxide (sold under the mark Remcopal 334) | 15 | g |
| Nonyl phenol oxyethylenated with 9 moles of ethylene oxide (sold under the mark Remcopal 349) | 12 | g |
| Oleic acid | 3 | g |
| Cetyl trimethyl ammonium bromide | 3 | g |
| Copra diethanolamide | 7 | g |
| Ethyl alcohol (96° titer) | 8 | g |
| Propylene glycol | 5 | g |
| Sodium bisulfite (35° Bé) | 1 | cc |
| Ammonia (20° Bé) | 5 | cc |
| Water, q.s.p. | 100 | g |

To 50 g of this composition there are added 50 g of hydrogen peroxide (20 volumes). The resulting mixture which is a gel is then applied to wet, dull hair having 80% blond hair and is permitted to remain in contact therewith for 20 minutes. After rinsing and shampooing a slightly ash natural blond color is obtained.

EXAMPLE 45

The following dye composition is prepared:

| | | |
|---|---|---|
| N,N-[di-β-hydroxyethyl] paraphenylene diamine semi-sulfate | 0.4 | g |
| 4-amino-2-methyl-N-(mesylamino ethyl) aniline sulfate | 0.3 | g |
| Para amino phenol | 0.3 | g |
| Meta diamino anisole sulfate | 0.04 | g |
| 6-hydroxy phenomorpholine | 0.08 | g |
| 2-acetylamino-3,5-dimethyl-4-hydroxy-4'-N,N-(di-β-hydroxy ethyl) amino diphenylamine | 0.08 | g |
| 2-amino-2'-chloro-4,4'-dihydroxy-5-methyl diphenylamine | 0.04 | g |
| Nonyl phenol oxyethylenated with 4 moles of ethylene oxide (sold under the mark Remcopal 334) | 15 | g |
| Nonyl phenol oxyethylenated with 9 moles of ethylene oxide (sold under the mark Remcopal 349) | 12 | g |
| Oleic acid | 3 | g |
| Cetyl trimethyl ammonium bromide | 3 | g |
| Copra diethanolamide | 7 | g |
| Ethyl alcohol (96° titer) | 8 | g |
| Propylene glycol | 5 | g |
| Sodium bisulfite (35° Bé) | 1 | cc |
| Ammonia (22° Bé) | 10 | cc |
| Water, q.s.p. | 100 | g |

To 50 g of this composition there are added 50 g of hydrogen peroxide (20 volumes). The resulting mixture is then applied to deep natural blond hair having 70% blond hair and is permitted to remain in contact therewith for 30 minutes. After rinsing and shampooing an ash blond color is obtained.

What is claimed is:

1. A hair dye composition in the form of an aqueous or hydroalcoholic solution, a cream, an emulsion, a dispersion or an aerosol comprising an oxidation dye and a diphenylamine selected from the group consisting of (i) a diphenylamine of the formula

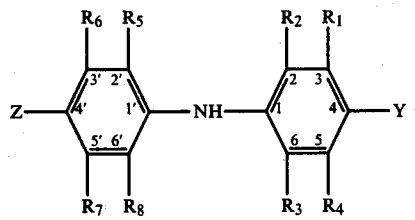

wherein

R$_1$ and R$_4$ each independently represent a member selected from the group consisting of hydrogen, halogen, lower alkyl having 1-6 carbon atoms, lower alkoxy having 1-6 carbon atoms, acetylamino and ureido;

R$_2$ and R$_3$ each independently represent a member selected from the group consisting of hydrogen, halogen, lower alkyl having 1-6 carbon atoms, lower alkoxy having 1-6 carbon atoms, amino, N-alkylamino wherein the alkyl moiety has 1-6 carbon atoms, N-hydroxyalkylamino wherein the alkyl moiety has 1-6 carbon atoms, acetylamino, N-carbamylalkylamino wherein the alkyl moiety has 1-6 carbon atoms and ureido;

R$_5$ represents a member selected from the group consisting of hydrogen, halogen, lower alkyl having 1-6 carbon atoms and lower alkoxy having 1-6 carbon atoms;

R$_6$, R$_7$ and R$_8$, each independently represent a member selected from the group consisting of hydrogen, halogen, lower alkyl having 1-6 carbon atoms and lower alkoxy having 1-6 carbon atoms;

Y represents a member selected from the group consisting of hydroxy and amino; and Z represents a member selected from the group consisting of hydroxy and

wherein

R$_9$ and R$_{10}$ each independently represent a member selected from the group consisting of hydrogen, lower alkyl containing 1-6 carbon atoms, hydroxyalkyl containing 1-6 carbon atoms, carbamyl alkyl wherein the alkyl moiety has 1-6 carbon atoms, amino alkyl wherein the alkyl moiety has 1-6 carbon atoms, monoalkylamino alkyl wherein each of the alkyl moieties has 1-6 carbon atoms, dialkylamino alkyl wherein each of the alkyl moieties has 1-6 carbon atoms, acylaminoalkyl wherein the alkyl moiety has 1-6 carbon atoms, alkylsulfonamido alkyl wherein each of the alkyl moieties has 1-6 carbon atoms, arylsulfonamidoalkyl wherein the alkyl moiety has 1-6 carbon atoms, sulfoalkyl wherein the alkyl moiety has 1-6 carbon atoms and piperidinoalkyl wherein the alkyl moiety has 1-6 carbon atoms, with the proviso that R$_2$ and R$_3$ are other than amino or acetylamino (1) when (a) Z is OH, (b) Y is amino and (c) each of R$_1$ and R$_4$ is hydrogen or alkyl or (2) when (d) Z is OH, (e) Y is amino, (f) R$_1$ or R$_4$ is alkoxy, and (g) each of R$_5$, R$_6$, R$_7$ and R$_8$ is hydrogen, alkyl or halogen, one of R$_5$, R$_6$, R$_7$ and R$_8$ being other than hydrogen, or (ii) a salt of the diphenylamine of (i), said diphenylamine and said oxidation dye being present in a tinctorially effective amount.

2. The composition of claim 1 wherein said oxidation dye is selected from the group consisting of paraphenylenediamine, para amino phenol and a heterocyclic base.

3. The composition of claim 2 wherein said paraphenylenediamine has the formula

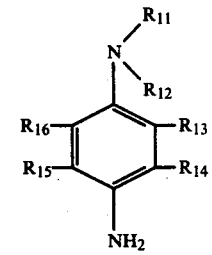

wherein

R$_{11}$ and R$_{12}$ each independently represent a member selected from the group consisting of hydrogen, straight or branch chained lower alkyl having 1-6 carbon atoms, hydroxy alkyl having 1-6 carbon atoms and one or more hydroxy groups, piperidinoalkyl wherein the alkyl moiety has 1-6 carbon atoms, carbamylalkyl wherein the alkyl moiety has 1-6 carbon atoms, dialkyl carbamylalkyl wherein each alkyl moiety has 1-6 carbon atoms, aminoalkyl having 1-6 carbon atoms, monoalkylaminoalkyl wherein each alkyl moiety has 1-6 carbon atoms, dialkylaminoalkyl wherein each alkyl moiety has 1-6 carbon atoms, ω-amino-sulfonylalkyl wherein the alkyl moiety has 1-6 carbon atoms, carboxyalkyl wherein the alkyl moiety has 1-6 carbon atoms, alkylsulfonamidoalkyl wherein each alkyl has 1-6 carbon atoms, arylsulfonamidoalkyl wherein the alkyl moiety has 1-6 carbon atoms, morpholinoalkyl wherein the alkyl moiety has 1-6 carbon atoms, acylaminoalkyl wherein the alkyl moiety has 1-6 carbon atoms and sulfoalkyl wherein the alkyl moiety has 1-6 carbon atoms, or R$_{11}$ and R$_{12}$ together with the nitrogen atom to which they are attached form a member selected from the group consisting of morpholino and piperidinyl; and R$_{13}$, R$_{14}$, R$_{15}$ and R$_{16}$ each independently represent a member selected from the group consisting of hydrogen, halogen, lower alkyl containing 1-6 carbon atoms and lower alkoxy containing 1-6 carbon atoms.

4. The composition of claim 2, wherein said paraphenylenediamine is selected from the group consisting of paraphenylenediamine, paratolylenediamine, methoxy paraphenylenediamine, chloroparaphenylenediamine, 2,6-dimethyl paraphenylenediamine, 2,5-dimethyl paraphenylenediamine, 2-methyl-5-methoxy paraphenylenediamine, 2,6-dimethyl-5-methoxy paraphenylenediamine, N,N-dimethyl paraphenylenediamine, 3-methyl-4-amino-N,N-(diethyl) aniline, N,N-(di-β-hydroxyethyl) paraphenylenediamine, 3-methyl-4-amino-N,N-

(di-β-hydroxyethyl) aniline, 3-chloro-4-amino-N,N-(di-β-hydroxyethyl) aniline, 4-amino-N,N-(ethyl, carbamylmethyl) aniline, 3-methyl-4-amino-N,N-(ethyl, carbamylmethyl) aniline, 4-amino-N,N-(ethyl, morpholinoethyl) aniline, 3-methyl-4-amino-N,N-(ethyl morpholinoethyl) aniline, 4-amino-N,N-(ethyl, acetylaminoethyl) aniline, 3-methyl-4-amino-N,N-(ethyl, acetylaminoethyl) aniline, 4-amino-N,N-(ethyl, mesylaminoethyl) aniline, 3-methyl-4-amino-N,N-(ethyl, mesylaminoethyl) aniline, 4-amino-N,N-(ethyl, β-sulfoethyl) aniline, 3-methyl-4-amino-N,N-(ethyl, β-sulfoethyl) aniline, N-[(4'-amino)phenyl]morpholine, N-[(4'-amino)phenyl]piperidine, 4-amino-N,N-(ethyl, piperidinoethyl) aniline, 3-methyl-4-amino-N-methyl aniline, 2-chloro-4-amino-N,N-(ethyl, sulfonamidoethyl) aniline, 2-chloro-4-amino-N-(ethyl) aniline and 2-methyl-4-amino-N-(β-hydroxyethyl) aniline.

5. The composition of claim 2 wherein said para amino phenol is selected from the group consisting of para amino phenol, 2-methyl-4-amino phenol, 3-methyl-4-amino phenol, 2-chloro-4-amino phenol, 3-chloro-4-amino phenol, 2,6-dimethyl-4-amino phenol, 3,5-dimethyl-4-amino phenol, 2,3-dimethyl-4-amino phenol and 2,5-dimethyl-4-amino phenol.

6. The composition of claim 2 wherein said heterocyclic base is selected from the group consisting of 2,5-diamino pyridine, 2-dimethyl amino-5-amino pyridine, 2-diethylamino-5-amino pyridine, 3-methyl-7-amino phenomorpholine and 5-amine indole.

7. The composition of claim 1 wherein said salt of the diphenylamine is selected from the group consisting of the hydrochloride, the hydrobromide and sulfate thereof.

8. The composition of claim 1 which also includes a coupler in an amount of about 0.001 to 5 percent by weight of the total composition.

9. The composition of claim 8 wherein said coupler has the formula

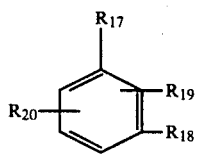

wherein
R$_{17}$ and R$_{18}$ each independently represent a member selected from the group consisting of hydroxy and —NHR wherein R represents a member selected from the group consisting of hydrogen, acyl, ureido, carbalkoxy wherein the alkoxy moiety has 1-6 carbon atoms, carbamylalkyl, wherein the alkyl moiety has 1-6 carbon atoms, alkyl having 1-6 carbon atoms, dialkylcarbamylalkyl wherein each alkyl moiety has 1-6 carbon atoms and hydroxy alkyl having 1-6 carbon atoms; R$_{17}$ and R$_{18}$ each independently can also represent a member selected from the group of hydrogen, alkoxy containing 1-6 carbon atoms and alkyl containing 1-6 carbon atoms with the proviso that at least one of R$_{17}$ and R$_{18}$ is hydroxy; and
R$_{19}$ and R$_{20}$ each independently represent a member selected from the group consisting of hydrogen, straight or branched alkyl containing 1-6 carbon atoms, alkoxy containing 1-6 carbon atoms, halogen, amino, aminoalkyl wherein the alkyl moiety has 1-6 carbon atoms, acylamino and ureido.

10. The composition of claim 9 wherein said coupler is selected from the group consisting of resorcinol, metaamino phenol, 2,4-diamino anisole, 2-methyl-5-ureido phenol, 2,6-dimethyl-5-amino phenol, 2-methyl-5-acetylamino phenol, 2,6-dimethyl-5-acetylamino phenol and 3-amino-4-methoxy phenol.

11. The composition of claim 8 wherein said coupler is a member selected from the group consisting of 6-hydroxy phenomorpholine, 6-amino phenomorpholine, a pyridine derivative, a diketone compound and a pyrazolone.

12. The composition of claim 1 which also includes a direct hair dye selected from the group consisting of an azo dye, an anthraquinone dye, a nitro-benzene dye, an indamine, an indoaniline and an indophenol.

13. The composition of claim 1 which also includes an effective amount of a glycol.

14. The composition of claim 13 wherein said glycol is selected from the group consisting of butyl glycol, propylene glycol and the monomethyl ester of diethylene glycol.

15. The composition of claim 1 wherein the alcohol of the hydroalcoholic solution is selected from the group consisting of ethanol and isopropanol.

16. The composition of claim 1 having a pH of about 5 to 11.

17. The composition of claim 16 wherein said pH ranges from about 8 to 10.

18. A composition comprising the hair dye composition of claim 1 in admixture with an oxidizing agent, said oxidizing agent being present in an amount ranging from 1–3 parts by weight per part by weight of said hair dye composition.

19. The composition of claim 18 wherein said oxidizing agent is selected from the group consisting of hydrogen peroxide, urea peroxide, a persulfate and a perborate.

20. The composition of claim 1 wherein said diphenylamine is present in an amount of about 0.01 to 3 percent by weight of the total composition.

21. The composition of claim 1 wherein said oxidation dye is present in an amount of about 0.03 to 2 percent by weight.

22. The composition of claim 8 wherein said coupler is present in an amount of about 0.015 to 1 percent by weight.

23. The composition of claim 1 which also includes an effective amount of a surface active agent.

24. The composition of claim 1 which also includes an effective amount of a cosmetic film forming resin.

25. The composition of claim 1 which also includes an effective amount of a reducing agent.

26. The composition of claim 1 which also includes an effective amount of a sequesterant.

27. The composition of claim 1 which also includes an effective amount of an alkalizing agent.

28. The composition of claim 1 which also includes an effective amount of an acidifying agent.

29. The hair dye composition of claim 1 wherein said diphenylamine is present in an amount of about 0.005 to 5 percent by weight of the total composition and said oxidation dye is present in an amount of about 0.001 to 5 percent by weight of the total composition.

30. The composition of claim 1, wherein said diphenylamine is present in an amount of about 0.005 to 5 percent by weight of the total composition.

31. The composition of claim 1, wherein said oxidation dye is present in an amount of about 0.001 to 5 percent by weight of the total composition.

32. A process for dyeing hair comprising impregnating hair to be dyed with the composition of claim 21 in an amount effective to dye said hair, permitting said composition to remain in contact with said hair for a period of time ranging from 5 to 40 minutes, rinsing said hair and shampooing said hair.

33. A hair dye composition comprising an aqueous or hydroalcoholic solution of an oxidation dye and a diphenylamine selected from the group consisting of (i) a diphenylamine of the formula

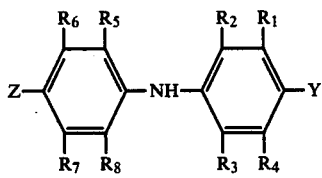

wherein

Y is hydroxy or amino, and $R_1$–$R_8$ and Z are selected from the combinations consisting of (a) $R_1$ is $CH_3$, $R_2$ is H, $R_3$ is $NH_2$, $R_4$ is H, $R_5$, $R_6$, $R_7$ and $R_8$ are each H and Z is N,N-dimethylamino, (b) $R_1$ is H, $R_2$ is $NH_2$, $R_3$ is H, $R_4$ is $OCH_3$, $R_5$, $R_6$, $R_7$ and $R_8$ are each H and Z is OH and (c) $R_1$ is H, $R_2$ is $NH_2$, $R_3$ is H, $R_4$ is $OCH_3$, $R_5$, $R_6$, $R_7$ and $R_8$ are each H and Z is N,N-(ethyl, carbamylmethyl) amino; and (ii) a salt of the diphenylamine of (i), said diphenylamine being present in an amount of about 0.005 to 5 percent by weight of the total composition and said oxidation dye being present in an amount of about 0.001 to 5 percent by weight of the total composition.

34. A hair dye composition comprising an aqueous or hydroalcoholic solution of an oxidation dye and a diphenylamine selected from the group consisting of (i) a diphenylamine of the formula

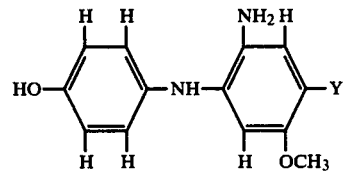

wherein

Y is hydroxy or amino; and (ii) a salt of the diphenylamine of (i), said diphenylamine being present in an amount of about 0.005 to 5 percent by weight of the total composition and said oxidation dye being present in an amount of about 0.001 to 5 percent by weight of the total composition.

* * * * *